(12) United States Patent
Ito et al.

(10) Patent No.: US 9,156,816 B2
(45) Date of Patent: Oct. 13, 2015

(54) TETRAZOLYLOXIME DERIVATIVE OR SALT THEREOF AND FUNGICIDE

(75) Inventors: Syuichi Ito, Odawara (JP); Ichirou Urihara, Odawara (JP); Hazumi Nomura, Odawara (JP); Yukuo Mukohara, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 246 days.

(21) Appl. No.: 13/579,105

(22) PCT Filed: Feb. 14, 2011

(86) PCT No.: PCT/JP2011/052995
§ 371 (c)(1),
(2), (4) Date: Aug. 15, 2012

(87) PCT Pub. No.: WO2011/105239
PCT Pub. Date: Sep. 1, 2011

(65) Prior Publication Data
US 2012/0309972 A1    Dec. 6, 2012

(30) Foreign Application Priority Data
Feb. 26, 2010 (JP) ................. 2010-043348

(51) Int. Cl.
| C07D 401/12 | (2006.01) |
| A01N 43/713 | (2006.01) |
| C07D 401/14 | (2006.01) |
| C07D 405/14 | (2006.01) |
| C07D 409/14 | (2006.01) |
| A01N 37/46 | (2006.01) |

(52) U.S. Cl.
CPC .............. *C07D 401/12* (2013.01); *A01N 37/46* (2013.01); *A01N 43/713* (2013.01); *C07D 401/14* (2013.01); *C07D 405/14* (2013.01); *C07D 409/14* (2013.01)

(58) Field of Classification Search
CPC ........................... C07D 401/12; A01N 43/713
See application file for complete search history.

(56) References Cited

U.S. PATENT DOCUMENTS

| 7,183,299 B2* | 2/2007 | Kobori et al. ............... 514/361 |
| 2010/0137594 A1* | 6/2010 | Kobori et al. ............... 544/333 |

FOREIGN PATENT DOCUMENTS

| JP | 2003-137875 | 5/2003 |
| JP | 2004-131392 | 4/2004 |
| JP | 2004-131416 | 4/2004 |
| JP | 2010-174008 | 8/2010 |
| JP | 2010-248273 | 11/2010 |
| JP | 2011-012088 | 1/2011 |
| JP | 2013-515702 | 5/2013 |
| WO | 03/016303 | 2/2003 |
| WO | 2009/020191 | 2/2009 |
| WO | 2009/090237 A2 | 7/2009 |
| WO | 2009/119072 | 10/2009 |
| WO | 2009/130900 A1 | 10/2009 |
| WO | 2010/000841 | 1/2010 |
| WO | 2010/000842 A1 | 1/2010 |
| WO | 2010/100876 A1 | 9/2010 |
| WO | 2011/080255 A2 | 7/2011 |
| WO | 2011/080256 A1 | 7/2011 |

OTHER PUBLICATIONS

Silverman, R.B. The Organic Chemistry of Drug Design and Drug Action 1992, Academic: New York, p. 19.*
International Search Report issued for PCT/JP2011/052995, dated Mar. 15, 2011, 4 pages (with English translation).
Office Action issued in JP Application No. 2012-501740, dated Jan. 7, 2014, 6 pages (with EN translation).
Supplementary European Search Report dated Jul. 10, 2013 in European Patent Application No. 11747203.5.
Supplementary European Search Report dated Jul. 3, 2013 in European Patent Application No. 11747203.5.

* cited by examiner

*Primary Examiner* — David K O Dell
(74) *Attorney, Agent, or Firm* — Kenyon & Kenyon, LLP

(57) ABSTRACT

There are provided a tetrazolyloxime derivative, a salt thereof, and a fungicide, that have excellent control effects against plant diseases. The fungicide contains, as an active ingredient, at least one selected from the group consisting of tetrazolyloxime derivatives represented by formula (6) and salts thereof. In formula (6), X represents a halogen atom, A represents a tetrazolyl group, R represents a halogen atom or the like, D represents a single bond or an oxygen atom, E represents a single bond or an alkylene chain, $R^{2a}$ and $R^{2b}$ each independently represents an alkoxy group or the like, and $R^3$ represents a hydrogen atom or an alkyl group.

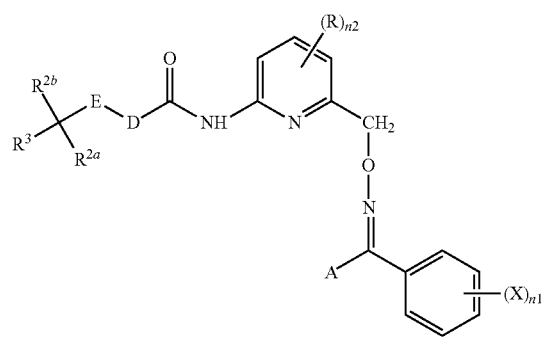

(6)

3 Claims, No Drawings

TETRAZOLYLOXIME DERIVATIVE OR SALT THEREOF AND FUNGICIDE

TECHNICAL FIELD

The present invention relates to a novel tetrazolyloxime derivative or a salt thereof, and a fungicide containing, as an active ingredient thereof, at least one selected therefrom.

The present application claims priority on the basis of Japanese Patent Application No. 2010-043348, filed in Japan on Feb. 26, 2010, the contents of which are incorporated herein by reference.

BACKGROUND ART

In the cultivation of agricultural and horticultural crops, numerous fungicides have been proposed for use against damage to those crops. However, since conventional fungicides have inadequate control effects against plant diseases, have limited use due to the appearance of chemical-resistant pathogens, cause chemical damage or contamination of plants, or demonstrate potent toxicity against humans, livestock and fish, these fungicides are not considered to always be satisfactory. Thus, there is a strong need for the development of a novel fungicide that has few of these disadvantages and can be used safely.

In relation to the present invention, the following Patent Documents 1 to 6 propose tetrazolyloxime derivatives having structures that resemble that of a compound according to the present invention, and the use thereof as a fungicide.

DOCUMENTS OF RELATED ART

Patent Documents

Patent Document 1: Japanese Unexamined Patent Application, First Publication No. 2004-131416
Patent Document 2: Japanese Unexamined Patent Application, First Publication No. 2004-131392
Patent Document 3: Japanese Unexamined Patent Application, First Publication No. 2003-137875
Patent Document 4: WO 2009/020191
Patent Document 5: WO 2003/016303
Patent Document 6: WO 2010/000841

SUMMARY OF THE INVENTION

Problems to be Solved by the Invention

An object of the present invention is to provide a novel tetrazolyloxime derivative or a salt thereof, having superior control effects against plant diseases, and a fungicide that contains, as an active ingredient thereof, at least one selected therefrom.

Means for Solving the Problems

In order to solve the aforementioned problems, the inventors of the present invention synthesized numerous tetrazolyloxime derivatives and conducted extensive studies on the physiological activity thereof. As a result, the inventors of the present invention found that a tetrazolyloxime derivative represented by formula (1), or a salt thereof, demonstrates superior control effects against plant diseases and eliminates concerns over chemical damage to useful plants. The present invention was completed on the basis of these findings.

Namely, the present invention includes the followings. [1] A tetrazolyloxime derivative represented by formula (1), or a salt thereof:

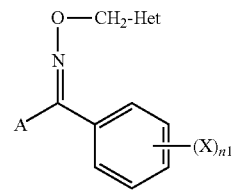

(in the formula (1),

X represents a halogen atom, C1-8 alkyl group, C1-8 alkoxy group, cyano group, C1-8 alkylsulfonyl group, nitro group, C1-8 haloalkyl group or unsubstituted or substituted aryl group, n1 indicates the number of X and represents an integer of 0 to 5, and X may be mutually the same or different when n1 is at least 2;

A represents a tetrazolyl group represented by formula (2) or formula (3):

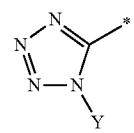

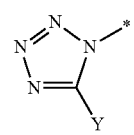

in the formula (2) and formula (3), Y represents a C1-8 alkyl group and asterisks (*) indicate bonding sites;

Het represents a group represented by formula (4) or formula (5):

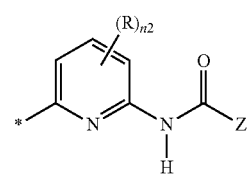

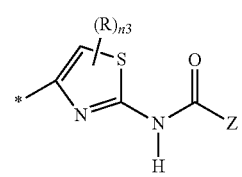

in the formula (4) and formula (5), asterisks (*) represent bonding sites;

R represents a halogen atom, cyano group, nitro group, hydroxyl group, thiol group, formyl group, carboxyl group, unsubstituted or substituted amino group, unsubstituted or substituted C1-8 alkyl group, unsubstituted or substituted C2-8 alkenyl group, unsubstituted or substituted C2-8 alkynyl group, unsubstituted or substituted aryl group, unsubstituted or substituted heterocyclic group, $OR^1$, $S(O)_mR^1$, $COR^1$ or $CO_2R^1$, $R^1$ represents an unsubstituted or substituted amino group, unsubstituted or substituted C1-8 alkyl group, unsubstituted or substituted C3-8 cycloalkyl group, unsubstituted or substituted C2-8 alkenyl group, unsubstituted or substituted C2-8 alkynyl group, unsubstituted or substituted aryl group or unsubstituted or substituted heterocyclic group, and m indicates the number of oxygen atoms in parentheses and represents an integer of 0 to 2;

n2 in the formula (4) indicates the number of R and represents an integer of 0 to 3, and a plurality of R may be mutually the same or different when n2 is at least 2;

n3 in the formula (5) indicates the number of R and represents 0 or 1;

Z in the formula (4) and formula (5) represents a C1-8 alkoxy C3-8 alkyl group, hydroxy C1-8 alkyl group, C3-8 cycloalkoxy group, C1-8 alkoxy C3-8 cycloalkoxy group, C2-4 alkoxy C3-5 alkoxy group, C1-8 alkoxy C1-8 haloalkoxy group, a group represented by formula (Z-1) or a group represented by formula (Z-2):

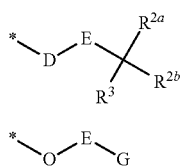

in the formula (Z-1) and formula (Z-2), asterisks (*) represent bonding sites;

E represents a single bond or C1-8 alkylene chain;

D represents a single bond or oxygen atom;

$R^{2a}$ and $R^{2b}$ respectively and independently represent a C1-8 alkoxy group, C1-8 haloalkoxy group, C1-8 alkoxy C1-8 alkoxy group, C1-8 alkylthio group, C1-8 haloalkylthio group or C1-8 alkoxy C1-8 alkylthio group and $R^{2a}$ and $R^{2b}$ may together form a ring;

$R^3$ represents a hydrogen atom or C1-8 alkyl group; and

G represents an unsubstituted or substituted saturated heterocyclic group).

[2] A tetrazolyloxime derivative represented by formula (6), or a salt thereof:

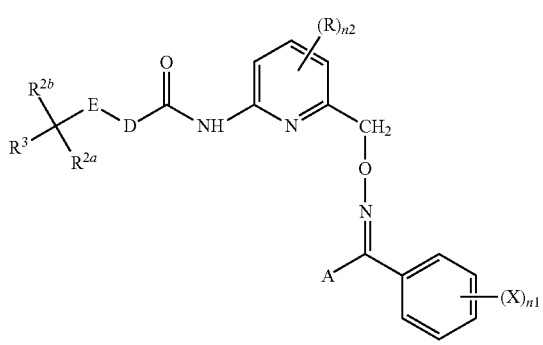

(in the formula (6), X, n1, A, R, n2, D, E, $R^{2a}$, $R^{2b}$ and $R^3$ are each the same as defined in the formula (1)).

[3] A fungicide containing, as an active ingredient thereof, at least one selected from the group consisting of the tetrazolyloxime derivatives and the salts thereof described in [1] or [2] above.

Furthermore, in the present specification, the nomenclature of "C1-8", for example, used to represent a functional group indicates that the number of carbon atoms that compose the group is 1 to 8.

Effects of the Invention

The tetrazolyloxime derivative and salt thereof according to the present invention demonstrate superior control effects against plant diseases and eliminate concerns over chemical damage to useful plants. Since the fungicide according to the present invention contains at least one selected from the group consisting of the tetrazolyloxime derivatives and the salts thereof according to the present invention, despite the control effects thereof being effective in the cultivation of agricultural crops, it does not cause chemical damage to crops or contaminate the environment, and has low toxicity with respect to humans, livestock and fish.

BEST MODE FOR CARRYING OUT THE INVENTION

The following provides a detailed explanation of the present invention by dividing into sections composed of: 1) tetrazolyloxime derivative or salt thereof, and 2) fungicide.

1) Tetrazolyloxime Derivative or Salt Thereof

The tetrazolyloxime derivative according to the present invention is a compound represented by formula (1), preferably a compound represented by formula (6).

In formula (1) or formula (6), X represents a halogen atom, C1-8 alkyl group, C1-8 alkoxy group, cyano group, C1-8 alkylsulfonyl group, nitro group, C1-8 haloalkyl group, or unsubstituted or substituted aryl group. Among these, X preferably represents a halogen atom.

Specific examples of the halogen atom include a fluorine atom, chlorine atom, bromine atom and iodine atom.

Specific examples of the C1-8 alkyl group include a methyl group, ethyl group, n-propyl group, i-propyl group, n-butyl group, i-butyl group, s-butyl group, t-butyl group, n-pentyl group and n-hexyl group.

Specific examples of the C1-8 alkoxy group include a methoxy group, ethoxy group, n-propoxy group, i-propoxy group, n-butoxy group, i-butoxy group, s-butoxy group, t-butoxy group and n-hexyloxy group.

Specific examples of the C1-8 alkylsulfonyl group include a methylsulfonyl group, ethylsulfonyl group, n-propylsulfonyl group, i-propylsulfonyl group and t-butylsulfonyl group.

Specific examples of the C1-8 haloalkyl group include a fluoromethyl group, chloromethyl group, bromomethyl group, difluoromethyl group, dichloromethyl group, trifluoromethyl group, trichloromethyl group, trifluoroethyl group, pentafluoroethyl group, 3,3,3,2,2-pentafluoropropyl group and 2,2,2-trifluoro-1-trifluoromethylethyl group.

The aryl group refers to a monocyclic or polycyclic aryl group. In the polycyclic aryl group, the remaining rings may be cyclanic rings, cyclenic rings, or aromatic rings, provided that at least one ring is an aromatic ring. The aryl group is preferably a C6-10 aryl group. Specific examples of the unsubstituted aryl group include a phenyl group, 1-naphthyl group, 2-naphthyl group, azulenyl group, indanyl group and tetralinyl group.

There are no particular limitations on substituents present in the substituted aryl group, provided that they are chemically acceptable. Specific examples of the substituents include the followings:

(1) halogen atoms such as a fluorine atom, chlorine atom, bromine atom or iodine atom; (2) alkyl groups such as a methyl group, ethyl group, n-propyl group, i-propyl group, n-butyl group, s-butyl group, i-butyl group, t-butyl group, n-pentyl group or n-hexyl group; (3) cycloalkyl groups such as a cyclopropyl group, cyclobutyl group, cyclopentyl group, cyclohexyl group or cycloheptyl group; (4) alkoxy groups such as a methoxy group, ethoxy group, n-propoxy group, i-propoxy group, n-butoxy group, i-butoxy group, s-butoxy group or t-butoxy group; (5) alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group; (6) cycloalkenyl groups such as a 2-cyclopropenyl group, 2-cyclopentenyl group, 3-cyclohexenyl group or 4-cyclooctenyl group; (7) alkenyloxy groups such as a vinyloxy group, allyloxy group, 1-propenyloxy group or 2-butenyloxy group; (8) alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group; (9) alkynyloxy groups such as an ethynyloxy group or propargyloxy group; (10) aryl groups such as a phenyl group, 1-napthyl group or 2-naphthyl group;

(11) aryloxy groups such as a phenoxy group or 1-naphthoxy group; (12) aralkyl groups such as a benzyl group or phenethyl group; (13) aralkyloxy groups such as a benzyloxy group or phenethyloxy group; (14) acyl groups such as a formyl group, acetyl group, propionyl group, benzoyl group, cyclohexylcarbonyl group or phthaloyl group; (15) alkoxycarbonyl groups such as a methoxycarbonyl group, ethoxycarbonyl group, n-propoxycarbonyl group, i-propoxycarbonyl group, n-butoxycarbonyl group or t-butoxycarbonyl group; (16) carboxyl groups; (17) hydroxyl groups; (18) haloalkyl groups such as a chloromethyl group, chloroethyl group, 1,2-dichloro-n-propyl group, 1-fluoro-n-butyl group, or perfluoro-n-pentyl group; (19) haloalkoxy groups such as a 2-chloro-n-propoxy group, 2,3-dichlorobutoxy group or trifluoromethoxy group; (20) haloalkenyl groups such as 2-chloro-1-propenyl group or 2-fluoro-1-butenyl group; (21) haloalkynyl groups such as a 4,4-dichloro-1-butynyl group, 4-fluoro-1-pentynyl group or 5-bromo-2-pentynyl group;

(22) haloalkenyloxy groups such as a 2-chloro-1-propenyloxy group or 3-bromo-2-butenyloxy group; (23) haloalkynyl groups such as a 3-chloropropargyl group or 3-iodopropargyl group; (24) haloalkynyloxy groups such as a 3-chloropropargyloxy group or 3-iodopropargyloxy group; (25) haloaryl groups such as 4-chlorophenyl group, 4-fluorophenyl group or 2,4-dichlorophenyl group; (26) haloaryloxy groups such as a 4-fluorophenoxy group or 4-chloro-1-naphthoxy group; (27) halogen-substituted acyl groups such as a chloroacetyl group, trifluoroacetyl group, trichloroacetyl group or 4-chlorobenzoyl group; (28) alkoxyalkyl groups such as a methoxymethyl group, ethoxymethyl group, 1-ethoxyethyl group or 2-ethoxyethyl group; (29) alkoxyalkoxy groups such as a methoxymethoxy group, ethoxymethoxy group, 1-ethoxyethoxy group or 2-ethoxyethoxy group; (30) a cyano group; (31) an isocyano group; (32) a nitro group; (33) an isocyanato group; (34) a cyanato group; (35) an amino group ($NH_2$ group); (36) alkylamino groups such as a methylamino group, dimethylamino group or diethylamino group; (37) arylamino groups such as an anilino group, naphthylamino group or anthranylamino group; (38) aralkylamino groups such as a benzylamino group or phenethylamino group; (39) alkylsulfonylamino groups such as a methylsulfonylamino group, ethylsulfonylamino group, n-propylsulfonylamino group, i-propylsulfonylamino group or n-butylsulfonylamino group; (40) arylsulfonylamino groups such as a phenylsulfonylamino group; (41) heteroarylsulfonylamino groups such as a piperazinylsulfonylamino group;

(42) acylamino groups such as a formylamino group, acetylamino group, propanoylamino group, butyrylamino group, i-propylcarbonylamino group or benzoylamino group; (43) alkoxycarbonylamino groups such as a methoxycarbonylamino group or ethoxycarbonylamino group; (44) haloalkylsulfonylamino groups such as a fluoromethylsulfonylamino group, chloromethylsulfonylamino group, bromomethylsulfonylamino group, difluoromethylsulfonylamino group, dichloromethylsulfonylamino group, 1,1-difluoroethylsulfonylamino group, trifluoromethylsulfonylamino group, 2,2,2-trifluoroethylsulfonylamino group or pentafluoroethylsulfonylamino group; (45) bis(alkylsulfonyl)amino groups such as a bis(methylsulfonyl)amino group, bis(ethylsulfonyl)amino group, (ethylsulfonyl)(methylsulfonyl)amino group, bis(n-propylsulfonyl)amino group, bis(i-propylsulfonyl)amino group, bis(n-butylsulfonyl)amino group or bis(t-butylsulfonyl)amino group;

(46) bis(haloalkylsulfonyl)amino groups such as a bis(fluoromethylsulfonyl)amino group, bis(chloromethylsulfonyl)amino group, bis(bromomethylsulfonyl)amino group, bis(dichloromethylsulfonyl)amino group, bis(1,1-difluoroethylsulfonyl)amino group, bis(trifluoromethylsulfonyl)amino group, bis(2,2,2-trifluoroethylsulfonyl)amino group or bis(pentafluoroethylsulfonyl)amino group; (47) unsubstituted or substituted hydrazino groups such as a hydrazino group, N'-phenylhydrazino group, N'-methoxycarbonylhydrazino group, N'-acetylhydrazino group or N'-methylhydrazino group; (48) unsubstituted or substituted aminocarbonyl groups such as an aminocarbonyl group, dimethylaminocarbonyl group, phenylaminocarbonyl group or N-phenyl-N-methylaminocarbonyl group; (49) unsubstituted or substituted hydrazinocarbonyl groups such as a hydrazinocarbonyl group, N'-methylhydrazinocarbonyl group or N'-phenylhydrazinocarbonyl group; (50) unsubstituted or substituted iminoalkyl groups such as an N-methyliminomethyl group, 1-N-phenyliminoethyl group, N-hydroxyiminomethyl group or N-methoxyiminomethyl group;

(51) a thiol group; (52) an isothiocyanato group; (53) a thiocyanato group; (54) alkylthio groups such as a methylthio group, ethylthio group, n-propylthio group, i-propylthio group, n-butylthio group, i-butylthio group, s-butylthio group or t-butylthio group; (55) alkenylthio groups such as a vinylthio group or allylthio group; (56) alkynylthio groups such as an ethynylthio group or propargylthio group; (57) arylthio groups such as a phenylthio group or naphthylthio group; (58) heteroarylthio groups such as a 2-pyridylthio group or 3-pyridazylthio group; (59) aralkylthio groups such as a benzylthio group or phenethylthio group; (60) heteroarylalkylthio groups such as a 2-pyridylmethylthio group or 2-furylmethylthio group; (61) alkylthiocarbonyl groups such as a methylthiocarbonyl group, ethylthiocarbonyl group, n-propylthiocarbonyl group, i-propylthiocarbonyl group, n-butylthiocarbonyl group, i-butylthiocarbonyl group, s-butylthiocarbonyl group or t-butylthiocarbonyl group;

(62) alkylthioalkyl groups such as amethylthiomethyl group or 1-methylthioethyl group; (63) arylthioalkyl groups such as a phenylthiomethyl group or 1-phenylthioethyl group; (64) alkylthioalkoxy groups such as a methylthiomethoxy group or 1-methylthioethoxy group; (65) arylthioalkoxy groups such as a phenylthiomethoxy group or 1-phenylthioethoxy group; (66) alkylsulfinyl groups such as a methylsulfinyl group, ethylsulfinyl group or t-butylsulfinyl group; (67) alkenylsulfinyl groups such as an allylsulfinyl group; (68) alkynylsulfinyl groups such as a propargylsulfinyl group; (69) arylsulfinyl groups such as a phenylsulfinyl group; (70) heteroarylsulfinyl groups such as a 2-pyridylsulfinyl group or 3-pyridylsulfinyl group; (71) aralkylsulfinyl groups such as a benzylsulfinyl group or phenethylsulfinyl group; (72) heteroarylalkylsulfinyl groups such as a 2-pyridylmethylsulfinyl group or 3-pyridylmethylsulfinyl group;

(73) alkylsulfonyl groups such as a methylsulfonyl group, ethylsulfonyl group or t-butylsulfonyl group; (74) alkenylsulfonyl groups such as an allylsulfonyl group; (75) alkynylsulfonyl groups such as a propargylsulfonyl group; (76) arylsulfonyl groups such as a phenylsulfonyl group; (77) heteroarylsulfonyl groups such as a 2-pyridylsulfonyl group or 3-pyridylsulfonyl group; (78) aralkylsulfonyl groups such as a benzylsulfonyl group or phenethylsulfonyl group; (79) heteroarylalkylsulfonyl groups such as a 2-pyridylmethylsulfonyl group or 3-pyridylmethylsulfonyl group; (80) unsaturated heterocyclic 5-membered ring groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group;

(81) unsaturated heterocyclic 6-membered ring groups such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group or 1,2,4-triazin-3-yl group; (82) saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, N-methylpiperazino group or oxazolin-2-yl group; (83) heterocyclooxy groups such as a 2-pyridyloxy group or 3-isoxazolyloxy group; (84) heteroarylalkyl groups such as a 2-pyridylmethyl group or 3-pyridylmethyl group; and, (85) heteroarylalkoxy groups such as a 2-pyridylmethoxy group or 3-pyridylmethoxy group.

These substituents exemplified in (1) to (85) may also further have substituents exemplified in (1) to (85) within a chemically acceptable range.

Specific examples of the substituted aryl group include a 4-fluorophenyl group, 4-chlorophenyl group, 2,4-dichlorophenyl group, 3,4-dichlorophenyl group, 3,5-dichlorophenyl group, 2,6-difluorophenyl group, 4-trifluoromethylphenyl group, 4-methoxyphenyl group, 3,4-dimethoxyphenyl group, 3,4-methylenedioxyphenyl group, 4-trifluoromethoxyphenyl group and 4-methoxy-1-napthyl group.

n1 indicates the number of X. n1 represents an integer of 0 to 5, preferably an integer of 0 to 3, and more preferably 0. Furthermore, X may be mutually the same or different when n1 is 2 or more.

A represents a tetrazolyl group represented by formula (2) or formula (3). Among these, a tetrazolyl group represented by formula (2) is preferable.

In formula (2) and formula (3), Y represents a C1-8 alkyl group. Examples of C1-8 alkyl groups are the same as those groups previously listed as examples of X.

Among these, Y is preferably a C1-3 alkyl group and particularly preferably a methyl group.

Het represents a group represented by formula (4) or formula (5). Among these, a group represented by formula (4) is preferable.

In formula (4) and formula (5), R represents a halogen atom, cyano group, nitro group, hydroxyl group, thiol group, formyl group, carboxyl group, unsubstituted or substituted amino group, unsubstituted or substituted C1-8 alkyl group, unsubstituted or substituted C2-8 alkenyl group, unsubstituted or substituted C2-8 alkynyl group, unsubstituted or substituted aryl group, unsubstituted or substituted heterocyclic group, $OR^1$, $S(O)_mR^1$, $COR^1$ or $CO_2R^1$.

Examples of the halogen atoms, unsubstituted C1-8 alkyl groups and unsubstituted or substituted aryl groups represented by R are the same those previously explained as examples of X.

Specific examples of the unsubstituted C2-8 alkenyl group represented by R include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group and 5-hexenyl group.

Specific examples of the unsubstituted C2-8 alkynyl group represented by R include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group and 1,1-dimethyl-2-butynyl group.

Specific examples of the unsubstituted heterocyclic group represented by R include unsaturated heterocyclic 5-membered ring groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group; unsaturated heterocyclic 6-membered ring groups such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group or 1,2,4-triazin-3-yl group; and, saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, piperazino group, N-methylpiperazino group, aziridino group, azetidino group, pyrrolidino group or oxazolin-2-yl group.

Examples of substituents in the substituted amino groups, substituted C1-8 alkyl groups, substituted C2-8 alkenyl groups, substituted C2-8 alkynyl groups and substituted heterocyclic groups represented by R are the same as those previously listed as examples of the substituents of substituted aryl groups represented by X within a chemically acceptable range.

Specific examples of the substituted amino group include a methylamino group, dimethylamino group, methylethylamino group, diethylamino group, t-butoxycarbonylmethylamino group, t-butoxycarbonylamino group, acetylmethylamino group, acetylethylamino group and benzoylmethylamino group.

Specific examples of the substituted C1-8 alkyl group include a chloromethyl group, methoxymethyl group, methylthiomethyl group, methylsulfonylmethyl group, dimethylaminomethyl group, trichloromethyl group, trifluoromethyl group and 2-chloroethyl group.

Specific examples of the substituted C2-8 alkenyl group include a 2-chloroethenyl group, 2-fluoroethenyl group, 3,3,3-trifluoro-1-pentenyl group, 1,2,2-trifluoroethenyl group, 2,3,3-trifluoro-2-propenyl group, 2,3,3-triiodo-2-propenyl group and 2-methoxyethenyl group.

Specific examples of the substituted C2-8 alkynyl group include a 2-chloroethynyl group, 2-fluoroethynyl group, 3-fluoro-1-propynyl group, 3,3,3-trifluoro-1-propynyl group, 3-fluoro-2-propynyl group and 3-iodo-2-propynyl group.

Specific examples of the substituted heterocyclic group include a 3-trifluoromethylpyridin-2-yl group, 4-trifluoromethoxy-2-pyridyl group, 3-methyl-1-pyrazolyl group, 4-trifluoromethyl-1-imidazolyl group and 3,4-difluoropyrrolidino group.

$R^1$ in $OR$, $S(O)_mR^1$, $COR^1$ and $CO_2R^1$ represented by R indicates an unsubstituted or substituted amino group, unsubstituted or substituted C1-8 alkyl group, unsubstituted or substituted C3-8 cycloalkyl group, unsubstituted or substituted C2-8 alkenyl group, unsubstituted or substituted C2-8 alkynyl group, unsubstituted or substituted aryl group, or unsubstituted or substituted heterocyclic group. In addition, m indicates the number of oxygen atoms in parentheses, and is an integer of 0 to 2.

Examples of the unsubstituted or substituted amino groups, unsubstituted or substituted C1-8 alkyl groups, unsubstituted or substituted C2-8 alkenyl groups, unsubstituted or substituted C2-8 alkynyl groups, unsubstituted or substituted aryl groups and unsubstituted or substituted heterocyclic groups are the same as those previously explained as examples of R.

Examples of the unsubstituted C3-8 cycloalkyl groups include a cyclopropyl group, cyclobutyl group, cyclopentyl group, cyclohexyl group and cycloheptyl group.

In addition, examples of substituents of the substituted C3-8 cycloalkyl groups represented by $R^1$ are the same as those previously indicated as examples of the substituents of the substituted aryl groups represented by X within a chemically acceptable range.

Specific examples of $OR^1$ include a methoxy group, ethoxy group, n-propoxy group, i-propoxy group, n-butoxy group, s-butoxy group, i-butoxy group, t-butoxy group, methoxymethoxy group, ethoxymethoxy group, methoxyethoxy group, ethoxyethoxy group, vinyloxy group, 1-propenyloxy group, 2-propenyloxy group, ethynyloxy group, 1-propynyloxy group, 2-propynyloxy group, aminooxy group, methylaminooxy group, diethylaminooxy group, methoxycarbonylaminooxy group, phenoxy group, trichloromethoxy group, trifluoromethoxy group, difluoromethoxy group, 2,2,2-trifluoroethoxy group, pentafluoroethoxy group and 2-fluoroethoxy group.

Specific examples of $S(O)_mR^1$ include a dimethylaminothio group, chloromethylthio group, 3-butenylthio group, ethynylthio group, 3-methylphenylthio group, methylsulfinyl group, ethylsulfinyl group, 1-butenylsulfinyl group, 1-hexynylsulfinyl group, 2,3-dimethylphenylsulfinyl group, methylsulfonyl group, dimethylaminosulfonyl group, N-ethyl-N-methylaminosulfonyl group, n-hexylsulfonyl group, 2-methyl-2-butenylsulfonyl group, 2-propynylsulfonyl group, 2-naphthylsulfonyl group, phenylsulfonyl group, 2-nitrophenylsulfonyl group and p-tolylsulfonyl group.

Specific examples of $COR^1$ include an acetyl group, benzoyl group, propanoyl group, i-propylcarbonyl group, t-butylcarbonyl group, cyclopropylcarbonyl group, cyclobutylcarbonyl group, cyclopentylcarbonyl group, vinylcarbonyl group, 1-propenylcarbonyl group, 2-propenylcarbonyl group, i-propenylcarbonyl group, 1-propynylcarbonyl group, 2-propynylcarbonyl group, 3-butenylcarbonyl group, methylaminocarbonyl group, dimethylaminocarbonyl group, N-methyl-N-ethylaminocarbonyl group, aziridinocarbonyl group, azetidinocarbonyl group, pyrrolidinocarbonyl group, piperidinocarbonyl group, morpholinocarbonyl group, piperazinocarbonyl group and N-methylpiperazinocarbonyl group.

Specific examples of $CO_2R^1$ include a methoxycarbonyl group, trifluoromethoxycarbonyl group, 1-pentenyloxycarbonyl group, 2-propynyloxycarbonyl group and phenoxycarbonyl group.

Among these, R is preferably a halogen atom, unsubstituted or substituted amino group, C1-8 alkyl group, $OR^1$ or $SR^1$.

The unsubstituted or substituted amino group is preferably an amino group ($NH_4$) or dialkylamino group, the C1-8 alkyl group is preferably a C1-4 alkyl group, $OR^1$ is preferably a C1-4 alkoxy group and $SR^1$ is preferably a C1-4 alkylthio group.

n2 in formula (4) indicates the number of R, and is an integer of any of 0 to 3, preferably 0. A plurality of R may be the same or different when n2 is 2 or more.

n3 in formula (5) indicates the number of R and is 0 or 1.

Z in formula (4) and formula (5) indicates a C1-8 alkoxy C3-8 alkyl group, hydroxy C1-8 alkyl group, C3-8 cycloalkoxy group, C1-8 alkoxy C3-8 cycloalkoxy group, C2-4 alkoxy C3-5 alkoxy group, C1-8 alkoxy C1-8 haloalkoxy group, a group represented by formula (Z-1) or a group represented by formula (Z-2).

(Z-1)

(Z-2)

The C1-8 alkoxy C3-8 alkyl group is a group in which at least one hydrogen atom of an alkyl group composed of 3 to 8 carbon atoms is substituted with an alkoxy group composed of 1 to 8 carbon atoms. Specific examples thereof include a methoxypropyl group, ethoxybutyl group, methoxybutyl group, methoxyhexyl group, propoxyoctyl group, 2-methoxy-1,1-dimethylethyl group and 1-ethoxy-1-methylethyl group.

The hydroxy C1-8 alkyl group is a group in which at least one hydrogen atom of an alkyl group composed of 1 to 8 carbon atoms is substituted with a hydroxyl group. Specific examples thereof include a hydroxymethyl group, hydroxyethyl group and 1-hydroxypropyl group.

The C3-8 cycloalkoxy group is a cycloalkoxy group composed of 3 to 8 carbon atoms. Specific examples thereof include a cyclopropyloxy group, cyclobutyloxy group, cyclopentyloxy group and cyclohexyloxy group.

The C1-8 alkoxy C3-8 cycloalkoxy group is a group in which at least one hydrogen atom of a cycloalkoxy group composed of 3 to 8 carbon atoms is substituted with an alkoxy group composed of 1 to 8 carbon atoms. Specific examples thereof include a 2-methoxycyclopropyloxy group, 1-ethoxycyclopropyloxy group, 2-butoxycyclobutoxy group and 3-hexyloxycyclohexyloxy group.

The C2-4 alkoxy C3-5 alkoxy group is a group in which at least one hydrogen atom of an alkoxy group composed of 3 to 5 carbon atoms is substituted with an alkoxy group composed of 2 to 4 carbon atoms. Specific examples thereof include a 3-ethoxypropoxy group, 2-ethoxybutoxy group, 4-butoxybutoxy group and 1-butoxypentoxy group.

The C1-8 alkoxy C1-8 haloalkoxy group is a group in which at least one hydrogen atom of a haloalkoxy group composed of 1 to 8 carbon atoms is substituted with an alkoxy group composed of 1 to 8 carbon atoms. Specific examples thereof include a fluoro(methoxy)methoxy group, dichloro(methoxy)methoxy group and 1,2-dibromo-3-methoxypropoxy group.

In formula (Z-1) and formula (Z-2), asterisks (*) indicate bonding sites.

In addition, E represents a single bond or C1-8 alkylene chain.

A C1-8 alkylene chain is an alkylene chain composed of 1 to 8 carbon atoms. Specific examples thereof include a methylene group, ethylene group, propylene group, butylene group, pentylene group and hexylene group.

In formula (Z-1), D represents a single bond or oxygen atom. In formula (Z-1), $R^{2a}$ and $R^{2b}$ respectively and independently represent a C1-8 alkoxy group, C1-8 haloalkoxy group, C1-8 alkoxy C1-8 alkoxy group, C1-8 alkylthio group, C1-8 haloalkylthio group or C1-8 alkoxy C1-8 alkylthio group. $R^{2a}$ and $R^{2b}$ may also together form a ring.

The C1-8 alkoxy group is an alkoxy group composed of 1 to 8 carbon atoms. Specific examples thereof include a methoxy group, ethoxy group, n-propoxy group, i-propoxy group, n-butoxy group, i-butoxy group, s-butoxy group, t-butoxy group and n-hexyloxy group.

The C1-8 haloalkoxy group is a group in which at least one hydrogen atom of a C1-8 alkoxy group is substituted with a halogen atom. Specific examples thereof include a 1-chloroethoxy group, 2,2-dichloroethoxy group and perfluorobutoxy group.

The C1-8 alkoxy C1-8 alkoxy group is a group in which at least one hydrogen atom of an alkoxy group composed of 1 to 8 carbon atoms is substituted with an alkoxy group composed of 1 to 8 carbon atoms. Specific examples thereof include a methoxymethoxy group, 2-methoxyethoxy group and 2-ethoxymethoxy group.

The C1-8 alkylthio group is an alkylthio group composed of 1 to 8 carbon atoms. Specific examples thereof include a methylthio group, ethylthio group, n-propylthio group, i-propylthio group, n-butylthio group, i-butylthio group, s-butylthio group and t-butylthio group.

The C1-8 haloalkylthio group is a group in which at least one hydrogen atom of a C1-8 alkylthio group is substituted with a halogen atom. Specific examples thereof include a 1-chloroethylthio group, trifluoromethylthio group, 2-bromoethylthio group and perfluoropropylthio group.

The C1-8 alkoxy C1-8 alkylthio group is a group in which at least one hydrogen atom of a C1-8 alkylthio group is substituted with an alkoxy group composed of 1 to 8 carbon atoms. Specific examples thereof include a 2-methoxyethylthio group, ethoxymethylthio group, 2-isopropoxyethylthio group, 2-methoxy-1-dimethylethylthio group and 1-ethoxy-1-methylethylthio group.

A ring formed by both $R^{2a}$ and $R^{2b}$ may have the same substituents as those listed as examples of the substituents of the aryl groups represented by X, and examples thereof include those having the structures represented by the following formulas. Asterisks (*) in the formulas indicate bonding sites.

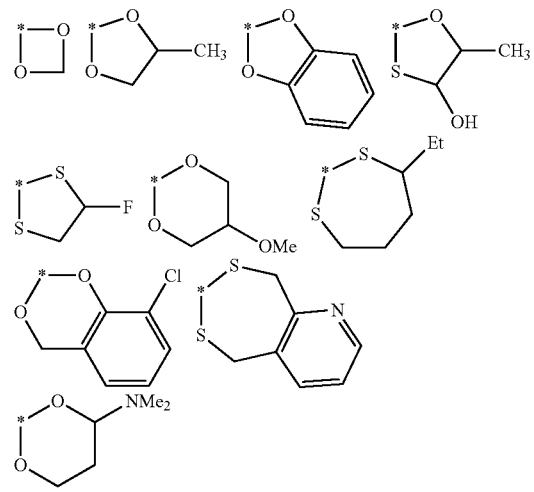

$R^3$ represents a hydrogen atom or C1-8 alkyl group.

Examples of the C1-8 alkyl group are the same those previously explained as examples of X.

In formula (Z-2), G represents an unsubstituted or substituted saturated heterocyclic group.

Specific examples of the saturated heterocyclic group include a pyrrolidinyl group, imidazolidinyl group, pyrazolidinyl group, piperidinyl group, piperazinyl group, qunuclidinyl group, morpholinyl group and tetrahydrofuranyl group.

Among these, Z is preferably the C2-4 alkoxy C3-5 alkoxy group or the group represented by formula (Z-1)

The tetrazolyloxime derivative according to the present invention probably demonstrates superior plant disease control effects not demonstrated by conventional tetrazolyloxime derivatives as a result of Het being the group represented by formula (4) or formula (5)

The tetrazolyloxime derivative represented by formula (1) has (E) form and (Z) form stereoisomers based on a carbon-nitrogen double bond of an oxime moiety. These two types of the stereoisomers and mixtures thereof are also included in the present invention. Normally, synthesized products are obtained in the form of the (Z) form only or as a mixture of the (E) form and the (Z) form. The mixture of the (E) form and the (Z) form may be respectively isolated into two isomers by separating and purifying by a known technique such as silica gel chromatography. Both the (Z) form and the (E) form have activity, and the (Z) form is particularly preferable.

A salt of the tetrazolyloxime derivative according to the present invention is a salt of a compound represented by formula (1). There are no particular limitations on the salt, provided that it is an agriculturally and horticulturally acceptable salt. Examples thereof include salts of inorganic acids such as hydrochlorides, nitrates or sulfates, and salts of organic acids such as acetates, lactates, propionates or benzoates.

(Method for Producing Tetrazolyloxime Derivative and Salt Thereof)

The tetrazolyloxime derivative represented by formula (1) may be produced in compliance with a method described in, for example, Japanese Unexamined Patent Application, First Publication No. 2003-137875 or International Publication No. WO 03/016303.

Namely, the tetrazolyloxime derivative according to the present invention as represented by formula (1) may be obtained by reacting a compound represented by formula (7) with a compound represented by formula (8) in the presence of a base.

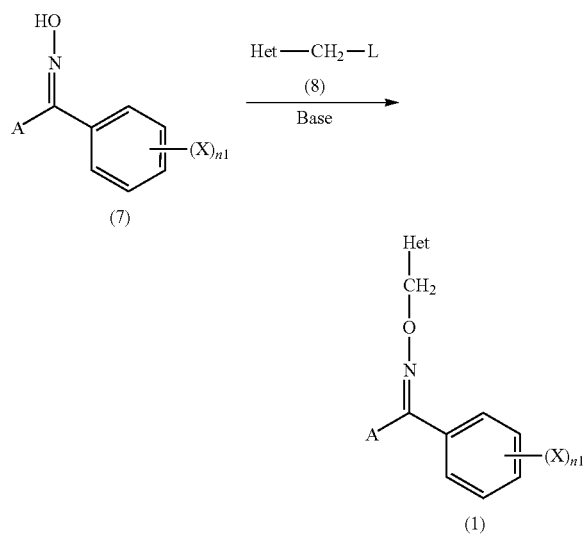

In formula (1), formula (7) and formula (8), A, X, Het and n1 are the same as previously defined, and L represents a leaving group such as a halogen atom.

Examples of the base used in the reaction include inorganic bases such as sodium hydroxide, potassium hydroxide, sodium hydride, sodium carbonate or potassium carbonate, and organic bases such as triethylamine, 4-(dimethylamino) pyridine, pyridine, 1,8-diazabicyclo[5.4.0]undec-7-ene (DBU) or 1,5-diazabicyclo[4.3.0]non-5-ene (DBN). One type of the bases may be solely used or at least two types thereof may be used in combination.

The amount of the base used is normally 0.01 moles to 100 moles and preferably 0.1 moles to 5 moles based on 1 mole of the compound represented by formula (7).

The reaction may be carried out in the presence or absence of a solvent.

There are no particular limitations on the solvent used, provided that it is an inert solvent in the reaction. Examples thereof include: hydrocarbon-based solvents such as pentane, hexane, heptane, benzene, toluene or xylene; halogen-based solvents such as dichoromethane, chloroform or carbon tetrachloride; nitrile-based solvents such as acetonitrile or propionitrile; ether-based solvents such as diethyl ether, dioxane or tetrahydrofuran; amide-based solvents such as N,N-dimethylformamide, N,N-dimethylacetamide or N-methylpyrrolidone; sulfoxide-based solvents such as dimethylsulfoxide; water; and mixed solvents thereof.

The temperature when carrying out the reaction is normally −70° C. to +20° C. and preferably −20° C. to +100° C. Although varying according to the reaction scale and the like, the reaction time is normally 30 minutes to 24 hours.

In addition, the salt of the compound represented by formula (1) may be produced by allowing an acid to act on the compound represented by formula (1) in accordance with routine methods.

The tetrazolyloxime derivative and the salt thereof according to the present invention may be produced by a method in which a compound represented by formula (9) or formula (10) is reacted instead of the compound represented by formula (8) using the same procedure as previously described to obtain a compound in which an amino-substituted pyridine group or an amino-substituted thiazoyl group has been introduced, followed by substituting the amino group for a group containing Z as previously described. Furthermore, $R^{40}$ and $R^{41}$ in formula (9) or formula (10) represent substituents such as a hydrogen atom or an alkyl group.

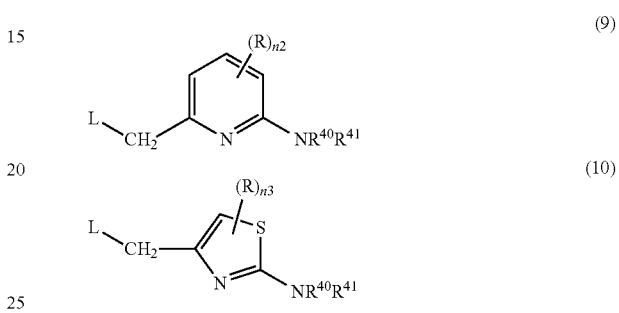

There are no particular limitations on the method used to substitute the amino group ($NR^{40}R^{41}$) for a group containing Z as previously described, and a known technique may be used.

In the above-mentioned reactions, the target compound represented by formula (1) and salt thereof may be isolated by carrying out an ordinary post-treatment procedure following completion of the reaction. In addition, if it is necessary to purify the product, conventionally known procedures may be performed, such as distillation, recrystallization or column chromatography.

The tetrazolyloxime derivative represented by formula (1) or the salt thereof (to be collective referred to as the "compound according to the present invention") possesses fungicidal action against a wide range of types of fungi, such as fungi belonging to Oomycetes, Ascomycetes, Deuteromycetes or Basidiomycetes.

Thus, a fungicide containing the compound according to the present invention as an active ingredient thereof may be used to control various plant diseases occurring during cultivation of agricultural and horticultural crops including flowering plants, lawn grasses, and pasture grasses, by seed treatment, foliar spraying, soil application, water surface application, or the like.

The fungicide may be used to control the followings, for example: Cercospora leaf spot (*Cercospora beticola*) or Aphanomyces root rot (*Aphanomyces cochlloides*) in sugar beets; brown leaf spot (*Mycosphaerella arachidis*) or leaf spot (*Mycosphaerella berkeleyi*) in peanuts; powdery mildew (*Sphaerotheca fuliginea*), gummy stem blight (*Mycosphaerella melonis*), Sclerotinia rot (*Sclerotinia sclerotiorum*), graymold (*Botrytis cinerea*), scab (*Cladosporium cucumerinum*), or downy mildew (*Pseudoperonospora cubensis*), in cucumbers; gray mold (*Botrytis cinerea*), leaf mold (*Cladosporium fulvum*), Pythium rot (*Pythium aphanidermatum*), or late blight (*Phytophthora infestans*), in tomatoes; gray mold (*Botrytis cinerea*), black rot (*Corynespora melongenae*), or powdery mildew (*Erysiphe cichoracearum*), in eggplants; damping-off (*Pythium ultimum*) in spinach; gray mold (*Botrytis cinerea*) or powdery mildew (*Sphaerotheca aphanis*) in strawberries; neck rot (*Botrytis allii*) or gray mold (*Botrytis*

*cinerea*) in onions; stem rot (*Sclerotinia sclerotiorum*) or gray mold (*Botrytis cinerea*) in kidney beans; powdery mildew (*Podosphaera leucotricha*), scab (*Venturia inaequalis*), or blossom blight (*Monilinia mali*), in apples; powdery mildew (*Phyllactinia kakicola*), anthracnose (*Gloeosporium kaki*), or angular leaf spot (*Cercospora kaki*), in persimmons; brown rot (*Monilinia fructicola*) in peaches and cherries; gray mold (*Botrytis cinerea*), powdery mildew (*Uncinula necator*), ripe rot (*Glomerella cingulata*), or downy mildew (*Plasmopara viticola*), in grapes; scab (*Venturia nashicola*), rust (*Gymnosporangium asiaticum*), or black spot (*Alternaria kikuchiana*), in pears; gray blight (*Pestalotia theae*) or anthracnose (*Colletotrichum theae-sinensis*) in tea leaves; scab (*Elsinoe fawcetti*), blue mold (*Penicillium italicum*), common green mold (*Penicillium digitatum*), or gray mold (*Botrytis cinerea*) in citrus; powdery mildew (*Erysiphe graminis* f. sp. *hordei*) or loose smut (*Ustilago nuda*) in barley; *Fusarium* blight (*Gibberella zeae*), leaf rust (*Puccinia recondita*), leaf spot (*Cochliobolus sativus*), glume blotch (*Leptosphaeria nodorum*), eyespot (*Pseudocercosporella herpotrichoides*), powdery mildew (*Erysiphe graminis* f. sp. *tritici*), pink snow mold (*Micronectriella nivalis*), or browning root rot (*Pythium iwayamai*), in wheat; blast (*Pyricularia oryzae*), sheath blight (*Rhizoctonia solani*), Bakanae disease (*Gibberella fujikuroi*), brown spot (*Cochliobolus niyabeanus*), or seedling blight (*Pythium graminicola*), in rice; purple stain (*Cercospora kikuchii*), downy mildew (*Peronospora manshurica*), or *Phytophthora* root and stemrot (*Phytophthora sojae*), in soybeans; late blight (*Phytophthora infestans*) in potatoes; clubroot (*Plasmodiophora brassicae*) in cruciferous plants; *Sclerotinia* stem-rot (*Sclerotinia sclerotiorum*), or powdery mildew (*Erysiphe cichoracearum*) in tobacco; gray mold (*Botrytis cinerea*) in tulips; *Sclerotinia* snow blight (*Sclerotinia borealis*) or bacterial shoot blight (*Pythium aphanidermatum*) in bent grass; powdery mildew (*Erysiphe graminis*) in orchard grass.

In addition, the compound according to the present invention is also effective against microorganisms that are resistant to metalaxyl such as *Phytophthora infestans* inpotatoes and tomatoes, *Pseudoperonospora cubensis* in cucumbers or *Plasmopara viticola* in grapes, as well as microorganisms that are resistant to strobilurin-based fungicides (such as kresoxim-methyl or azoxystrobin) such as *Pseudoperonospora cubensis* in cucumbers or *Plasmopara viticola* in grapes.

Examples of diseases for which application of the compound according to the present invention is preferable include numerous types of diseases caused by Oomycetes as exemplified by *Plasmopara viticola* in grapes, *Pseudoperonospora cubensis* in gourds, *Phytophthora infestans* in potatoes and tomatoes, *Pythium aphanidermatum* in grasses and *Aphanomyces cochlioides* in sugar beets.

The compound according to the present invention may also be used as an anti-fouling agent for preventing adhesion of aquatic organisms to articles submerged in water such as boat bottoms or fish nets.

In addition, some intermediates produced in the production process of the compound according to the present invention demonstrate fungicidal activity.

Moreover, the compound according to the present invention may also be used as a fungicide or anti-mold agent of walls, bathtubs, shoes or clothing by mixing the compound into paint, fibers, or the like.

2) Fungicide

The fungicide according to the present invention contains, as an active ingredient thereof, at least one compound selected from the group consisting of the tetrazolyloxime derivatives represented by formula (1) or the salts thereof.

The fungicide according to the present invention may consist only of the compound according to the present invention or may consist of the compound according to the present invention and other components.

The fungicide according to the present invention may be formulated in a form able to be adopted by an ordinary agricultural chemical, such as a wettable powder, granule, powder, emulsion, aqueous solution, suspension or flowable agent.

Additives and/or carriers may be used in solid preparations, examples of which include vegetable powders such as soybean powder or wheat powder, mineral fine powders such as diatomaceous earth, apatite, gypsum, talc, bentonite, pyrophyllite or clay, and organic or inorganic compounds such as sodium benzoate, urea or sodium sulfate.

Solvents such as oil fractions such as kerosene, xylene, or solvent naphtha, cyclohexane, cyclohexanone, dimethylformamide, dimethylsulfoxide, alcohol, acetone, trichloroethylene, methyl isobutyl ketone, mineral oil, vegetable oil or water may be used in liquid preparations.

Moreover, a surfactant may be added to the fungicide according to the present invention as necessary to obtain a uniform and stable form. Examples of the surfactant include: nonionic surfactants such as polyoxyethylene-added alkyl phenyl ethers, polyoxyethylene-added alkyl ethers, polyoxyethylene-added higher fatty acid esters, polyoxyethylene-added sorbitan higher fatty acid esters, or polyoxyethylene-added tristyryl phenyl ether; sulfuric acid ester salts of polyoxyethylene-added alkyl phenyl ethers, alkyl benzene sulfonates, sulfuric acid ester salts of higher alcohols, alkyl naphthalene sulfonates, polycarboxylates, lignin sulfonates, formaldehyde condensates of alkyl naphthalene sulfonates and i-butylene-maleic anhydride copolymers.

Although there are no particular limitations on the amount of the active ingredient in the fungicide, the amount is preferably 0.5% by mass to 95% by mass and more preferably 2% by mass to 70% by mass based on the total mass of the fungicide.

In the case the fungicide according to the present invention is a wettable powder, emulsion or flowable agent, it may be used as a suspension or emulsion by diluting with water to a prescribed concentration. In addition, in the case the fungicide according to the present invention is a powder or granules, it may be used by directly spraying onto plants.

In the case of applying a wettable powder, emulsion, suspension, solution or water-dispersible granules with water, the applied concentration is 1 ppm to 1000 ppm and preferably 10 ppm to 250 ppm.

Although the applied amount of the fungicide according to the present invention varies according to weather conditions, preparation form, application time, application method, applied location, target control disease, target crop, or the like, the applied amount is normally 1 g to 1,000 g and preferably 10 g to 100 g as the amount of the active ingredient compound per hectare.

The fungicide according to the present invention may be used by mixing with other fungicides, insecticides, miticides, plant growth regulators, or the like.

Typical examples of other fungicides, insecticides, miticides and plant growth regulators able to be used by mixing with the fungicide according to the present invention include the followings.

<Fungicides>

Copper agents: basic copper chloride, basic copper sulfate, or the like.

Sulfur agents: thiuram, zineb, maneb, mancozeb, ziram, propineb, polycarbamate, or the like.

Polyhaloalkylthio agents: captan, folpet, dichlorfluanid, or the like.

Organic chlorine agents: chlorothalonil, fthalide, or the like.

Organic phosphorous agents: IBP, EDDP, tolclophos-methyl, pyrazophos, fosetyl, or the like.

Benzimidazole agents: thiophanate-methyl, benomyl, carbendazim, thiabendazole, or the like.

Dicarboxylmide agents: iprodione, procymidone, vinclozolin, fluoroimide, or the like.

Carboxyamide agents: oxycarboxin, mepronil, flutolanil, techlofthalam, trichlamide, pencycuron, or the like.

Acyalanine agents: metalaxyl, oxadixyl, furalaxyl, or the like.

Strobilurin-based fungicides: azoxystrobin, kresoxim-methyl, pyraclostrobin, trifloxystrobin, pyribencarb, famoxadone, fenamidone, or the like.

Anilinopyrimidine agents: andoprin, mepanipyrim, pyrimethanil, cyprodinil, or the like.

SBI agents: triadimefon, triadimenol, bitertanol, miclobutanil, hexaconazol, propiconazole, triflumizole, prochloraz, pefurazoate, fenarimol, pyrifenox, triforine, flusilazole, etaconazole, diclobutrazol, fluotrimazole flutriafen, penconazole, diniconazole, imazalil, tridemorph, fenpropimorph, buthiobate, epoxyconazole, metconazole, prothioconazole, spiroxamine, fenhexamid, pyributicarb, or the like.

Anrtibiotic agents: polyoxin, blasticidin S, kasugamycin, validamycin, dihydrostreptomycin sulfate, or the like.

Anilide-based agents: boscalid, penthiopyrad, fluopyram, bixafen, or the like.

Guanidine-based agents: iminoctadine hydrochloride, iminoctadine albesilate, dodine, guazatine, or the like.

Valine-based agents: dimethomorph, flumorph, iprovalicarb, benthiavalicarb, mandipropamide, or the like.

Other fungicides: cymoxanii, cyazofamid, amisulbrom, propamocarb, fluazinam, propamocarb acetate, etapoxam, fluopicolid, zoxamide, cyflufenamid, metrafenone, proquinazid, hydroxyisoxazole, metasulfocarb, anilazine, isoprothiolane, ferimzone, probenazole, tiadinil, acibenzolar-S-methyl, isotianil, pyroquilon, fthalide, tricyclazole, carpropamide, fenoxanil, diclocymet, fluazinam, fludioxonil, pyrrolnitrin, hydroxyisoxazole, flusulfamide, diethofencarb, quintozene, metasulfocarb, anilazine, chinomethionate, dithianon, dinocap, diclomezine, oxolinic acid, lecithin, sodium bicarbonate, fenaminosulf, phenazine oxide, or the like.

<Insecticide/Miticides>

Organic phosphorous and carbamate-based insecticides: fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydemetone methyl, ethion, salithion, cyanophos, isoxathion, pyridafenthion, phosalone, methidathion, sulprofos, chlorfenvinphos, tetrachlorovinphos, dimethylvinphos, propaphos, isofenphos, ethyl thiometon, profenofos, pyraclofos, monocrotophos, azinphos-methyl, aldicarb, methomyl, thiodicarb, carbofuran, carbosulphan, benfuracarb, furathiocarb, propoxur, BPMC, MTMC, MIPC, carbaryl, pirimicarb, ethiophencarb, phenoxycarb, or the like.

Pyrethroid-based insecticides: permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen, flufenprox, acrinathrin, or the like.

Benzoylurea-based other insecticides: diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulfate, rotenone, metaldehyde, emamectin, flubendiamide, spinosad, machine oil, microbial agrichemicals such as BT or insect pathogenic viruses, or the like.

Nematocides: fenamiphos, fosthiazate, or the like.

Miticides: chlorobenzilate, phenisobromolate, dicofol, amitraz, BPPS, benzomate, hexythiazox, fenbutatin oxide, polynactin, chinomethionate, CPCBS, tetradifon, avermectin, milbemectin, clofentezine, cyhexatin, pyridaben, fenpyroximate, tebufenpyrad, pyrimidifen, fenothiocarb, dienochlor, fluacrypyrim, or the like.

<Plant Growth Regulators>

Gibberellins (such as gibberellin A3, gibberellin A4, gibberellin A7), IAA, NAA, or the like.

EXAMPLES

The present invention will be explained in more detail by indicating examples thereof. However, the present invention is not limited to the examples.

Experiment Example 1

Production of (Z)-(1-methyl-1H-tetrazol-5-yl)phenylmethanone-o-[2-(2,2-dimethoxyethanecarbonylamino)pyridin-6-ylmethyl]oxime

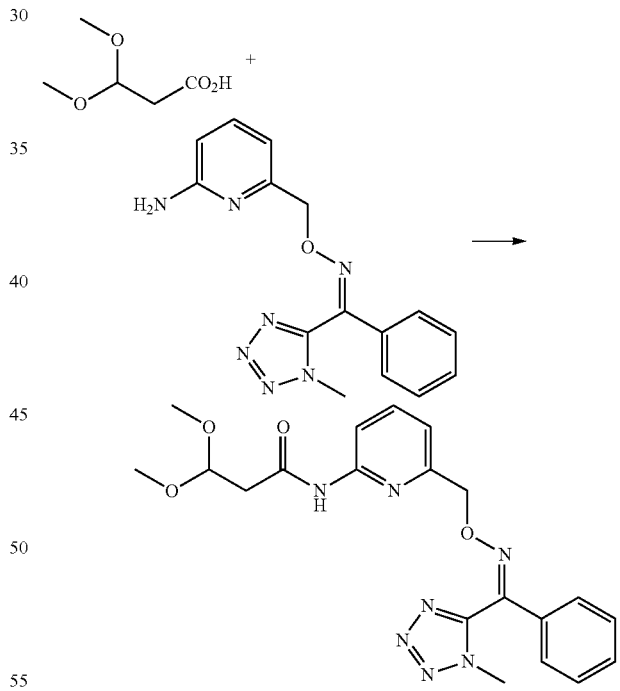

0.18 g (1.35 mmol) of 3,3-dimethoxy-propionate were dissolved in 10 ml of methylene chloride followed by the addition of 0.16 g (1.35 mmol) of pivaloyl chloride and 0.16 g (1.50 mmol) of triethylamine and stirring for 30 minutes at room temperature. Next, 0.14 g (0.45 mmol) of (Z)-(1-methyl-1H-tetrazol-5-yl)phenylmethanone-o-[2-aminopyridin-6-ylmethyl]oxime were added followed by stirring overnight at room temperature. After distilling off the solvent, the resulting crude product was purified by silica gel column chromatography (eluent: hexane:methyl acetate=1:1 (v/v)) to obtain 0.13 g of the target compound.

Experiment Example 2

Production of (Z)-(1-methyl-1H-tetrazol-5-yl)phenylmethanone-o-[2-(2-methyl-1,3-dioxan-2-yl-carbonylamino)pyridin-6-ylmethyl]oxime

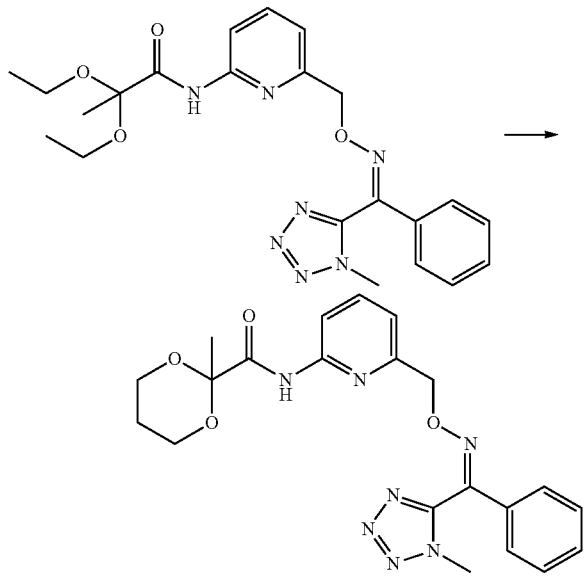

0.50 g (1.10 mmol) of (Z)-(1-methyl-1H-tetrazol-5-yl)phenylmethanone-o-[2-(1,1-diethoxyethanecarbonylamino)pyridin-6-ylmethyl]oxime produced using a procedure similar to that of Experiment Example 1 were dissolved in 20 ml of toluene followed by the addition of 0.10 g (1.32 mmol) of 1,3-propanediol and 0.05 g (0.29 mmol) of p-toluenesulfonate and refluxing while heating overnight. After distilling off the solvent, the resulting crude product was purified by silica gel column chromatography to obtain 0.38 g of the target compound.

Experiment Example 3

Production of (Z)-(1-methyl-1H-tetrazol-5-yl)phenylmethanone-o-[2-(2,2-dimethoxyethoxycarbonylamino)pyridin-6-ylmethyl]oxime i) Production of (Z)-(1-methyl-1H-tetrazol-5-yl)phenylmethanone-o-[2-(phenoxycarbonylamino)pyridin-6-ylmethyl]oxime

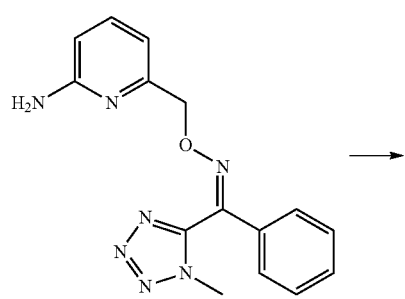

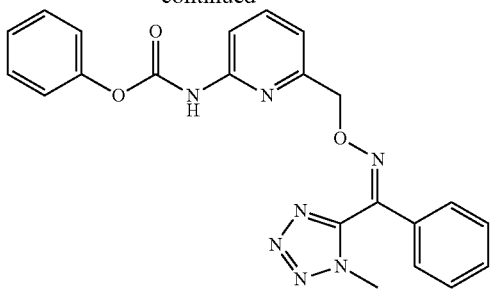

5.59 g (18.07 mmol) of (Z)-(1-methyl-1H-tetrazol-5-yl)phenylmethanone-o-(2-aminopyridin-6-ylmethyl) oxime and 1.79 g (22.58 mmol) of pyridine were dissolved in methylene chloride (80 mL) followed by adding dropwise a methylene chloride solution (50 mL) containing 3.53 g (22.58 mmol) of phenyl chloroformate over the course of 1 hour. Following completion of dropwise addition, the reaction solution was stirred for 18 hours at room temperature. Methylene chloride (200 mL) and water (100 mL) were then added to the reaction solution and an organic phase was washed with a saturated saline solution followed by drying by the addition of magnesium sulfate and concentrating under reduced pressure. The resulting crude product was purified by silica gel column chromatography (eluent: hexane:ethyl acetate=4:1 (v/v)) to obtain 6.12 g of the target compound.

ii) Production of (Z)-(1-methyl-1H-tetrazol-5-yl)phenylmethanone-o-[2-(2,2-dimethoxyethoxycarbonylamino)pyridin-6-ylmethyl]oxime

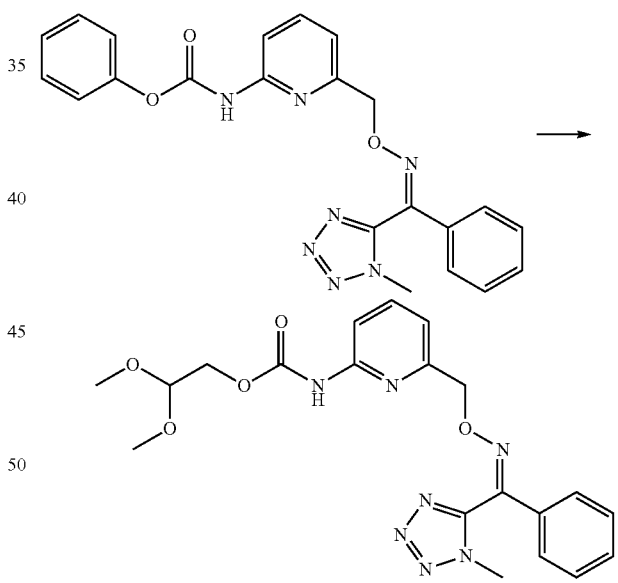

0.25 g (0.58 mmol) of (Z)-(1-methyl-1H-tetrazol-5-yl)phenylmethanone-o-[2-(phenoxycarbonylamino)pyridin-6-ylmethyl]oxime and 0.12 g (1.16 mmol) of 2,2-dimethoxyethanol were dissolved in tetrahydrofuran (5 mL) followed by the addition of 0.11 g (0.70 mmol) of 1,8-diazabicyclo[5.4.0]undec-7-ene and stirring for 2 days at room temperature. The reaction solution was then concentrated under reduced pressure. The resulting crude product was purified by silica gel column chromatography to obtain 0.25 g of the target compound.

Examples of the tetrazolyloxime derivative according to the present invention that may be produced using procedures similar to those mentioned above are listed in Tables 1 to 5.

The units of melting point (mp) indicated in physical property columns of the tables are ° C. The term "VISC. OIL" indicates a viscous oil, and the term "AMR" indicates an amorphous compound. In addition, the term "nD20.7 1.5438", for example, indicates that the refractive index at 20.7° C. is 1.5438.

Furthermore, Tables 1 to 5 merely indicate a portion of the tetrazolyloxime derivative according to the present invention that may be produced using procedures similar to those mentioned above. It may be easily understood by a person with ordinary skill in the art from the descriptions of the present description that other compounds unable to be specifically indicated in the present description, namely those substituted with various groups that do not deviate from the purport and scope according to the present invention, can also be produced and used.

TABLE 1

| Compound No. | Chemical structure | Physical property | $^1$H-NMR |
|---|---|---|---|
| a-1 | 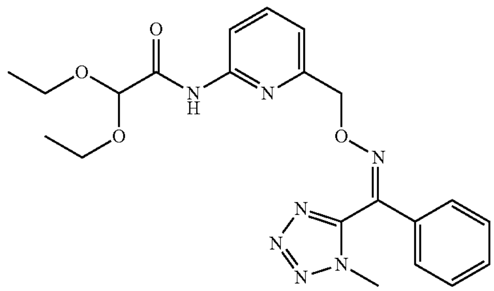 | VISC. OIL | 1.30 (t, 6H), 3.65-3.81 (m, 4H), 4.00 (s, 3H), 4.93 (s, 1H), 5.29 (s, 2H), 7.04 (d, 1H), 7.34-7.53 (m, 5H), 7.72 (t, 1H), 8.19 (d, 1H), 8.85 (br-s, 1H) |
| a-2 | 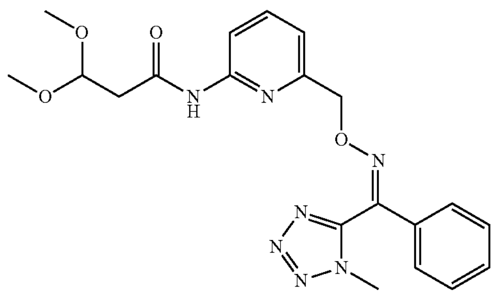 [SMILES: COC(CC(=O)Nc1cccc(CO/N=C(/c2ccccc2)c2nnnn2C)n1)OC] | VISC. OIL | 2.75 (d, 2H), 3.50 (s, 6H), 3.99 (s, 3H), 4.77 (t, 1H), 5.27 (s, 2H), 7.00 (d, 1H), 7.34-7.53 (m, 5H), 7.68 (t, 1H), 8.12 (d, 1H), 8.54 (br-s, 1H) |
| a-3 | 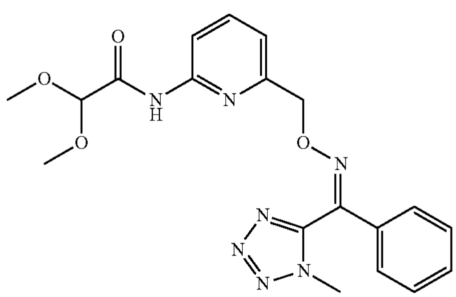 [SMILES: COC(OC)C(=O)Nc1cccc(CO/N=C(/c2ccccc2)c2nnnn2C)n1] | mp 88-90 | — |
| a-4 | 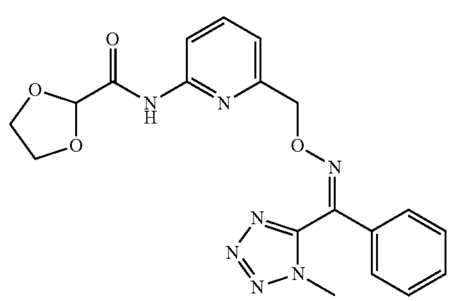 [SMILES: Cn1nnnc1/C(=N\OCc1cccc(NC(=O)C2OCCO2)n1)c1ccccc1] | VISC. OIL | 3.99 (s, 3H), 4.04-4.17 (m, 4H), 5.29 (s, 2H), 5.30 (s, 1H), 7.06 (d, 1H), 7.35-7.52 (m, 5H), 7.73 (t, 1H), 8.18 (d, 1H), 8.75 (br-s, 1H) |

TABLE 1-continued

| Compound No. | Chemical structure | Physical property | ¹H-NMR |
|---|---|---|---|
| a-5 | 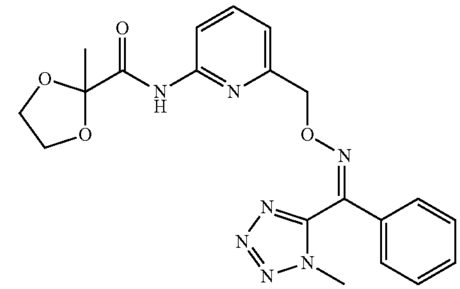 [SMILES: Cn1nnnc1/C(=N\OCc1cccc(NC(=O)C2(C)OCCO2)n1)c1ccccc1] | AMR | 1.65 (s, 3H), 4.00 (s, 3H), 402-4.16 (m, 4H), 5.29 (s, 2H), 7.05 (d, 1H), 7.35-7.53 (m, 5H), 7.73 (t, 1H), 8.20 (d, 1H), 8.90 (br-s, 1H) |
| a-6 | 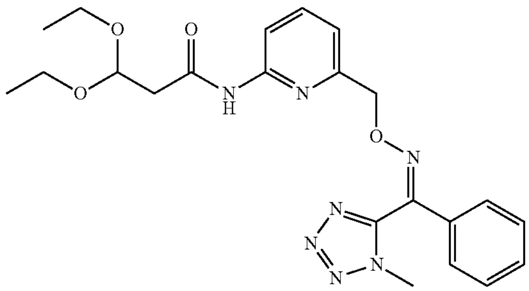 [SMILES: CCOC(CC(=O)Nc1cccc(CO/N=C(/c2ccccc2)c2nnnn2C)n1)OCC] | VISC. OIL | 1.26 (t, 6H), 2.74 (d, 2H), 3.55-3.98 (m, 4H), 4.08 (s, 3H), 4.89 (t, 1H), 5.26 (s, 2H), 6.99 (d, 1H), 7.34-7.52 (m, 5H), 7.68 (t, 1H), 8.11 (d, 1H), 8.84 (br-s, 1H) |
| a-7 | 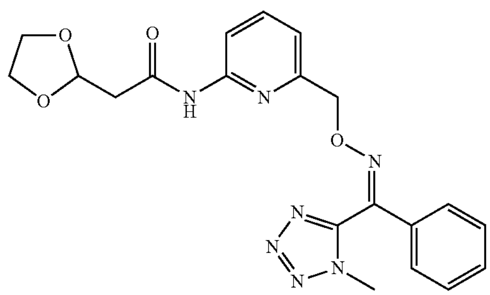 [SMILES: Cn1nnnc1/C(=N\OCc1cccc(NC(=O)CC2OCCO2)n1)c1ccccc1] | VISC. OIL | 2.82 (d, 2H), 3.89-4.16 (m, 4H), 3.99 (s, 3H), 5.25 (t, 1H), 5.27 (s, 2H), 7.01 (d, 1H), 7.34-7.52 (m, 5H), 7.69 (t, 1H), 8.14 (d, 1H), 8.69 (br-s, 1H) |
| a-8 | 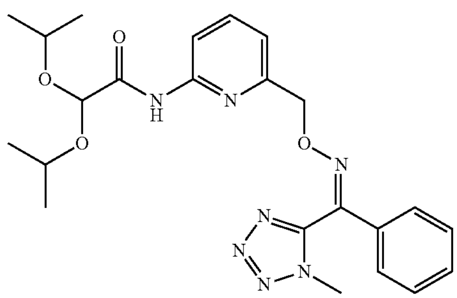 [SMILES: CC(C)OC(OC(C)C)C(=O)Nc1cccc(CO/N=C(/c2ccccc2)c2nnnn2C)n1] | nD 20.7 1.5438 | — |
| a-9 | 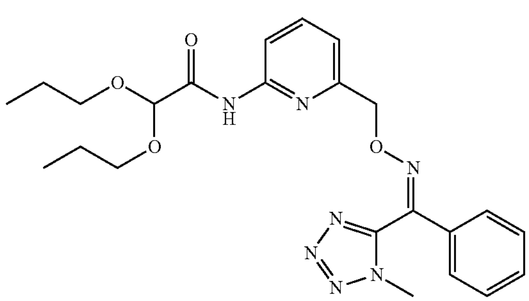 [SMILES: CCCOC(OCCC)C(=O)Nc1cccc(CO/N=C(/c2ccccc2)c2nnnn2C)n1] | nD 20.7 1.5490 | — |

TABLE 1-continued

| Compound No. | Chemical structure | Physical property | ¹H-NMR |
|---|---|---|---|
| a-10 | 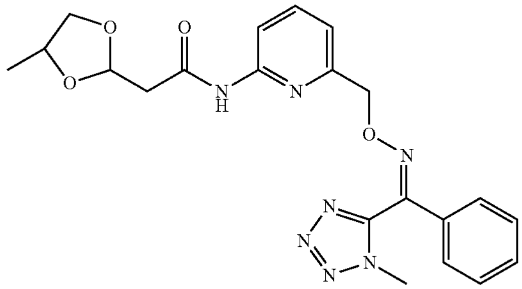 [SMILES: CC1COC(CC(=O)Nc2cccc(CO/N=C(/c3ccccc3)c3nnnn3C)n2)O1] | VISC. OIL | A:B = 4:6 diastereomer mixture 1.30(A) & 1.34 (B) (d, 3H), 2.79(A) & 2.83(B) (d, 2H), 3.46-3.55 (A&B) (m, 1H), 3.99 (A&B) (s, 3H), 3.99-4.34 (A&B) (m, 2H), 5.27 (A&B) (s, 2H), 5.30(A) & 5.41(B) (t, 1H), 7.00 (A&B) (d, 1H), 7.35-7.52 (A&B) (m, 5H), 7.70 (A&B) (t, 1H), 8.15 (A&B) (d, 1H), 8.84 (A&B) (br-s, 1H) |
| a-11 | 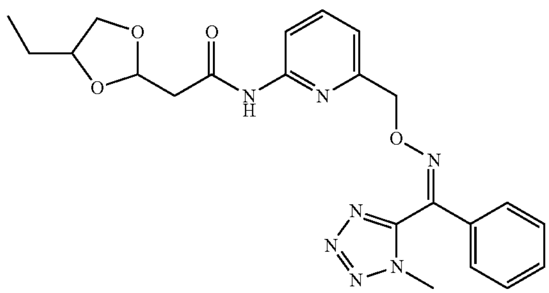 [SMILES: CCC1COC(CC(=O)Nc2cccc(CO/N=C(/c3ccccc3)c3nnnn3C)n2)O1] | VISC. OIL | A:B = 1:1 diastereomer mixture 0.98 (A&B) (t, 3H), 1.50-175 (A&B) (m, 2H), 2.79(A) & 2.83(B) (d, 2H), 3.55-3.64 (A&B) (m, 1H), 3.98 (A&B) (s, 3H), 3.99-4.22 (A&B)(m, 2H), 5.27 (A&B) (s, 2H), 5.28(A) & 5.36(B) (t, 1H), 7.00 (A&B) (d, 1H), 7.35-7.53 (A&B) (m, 5H), 7.69 (A&B) (t, 1H), 8.15 (A&B) (d, 1H), 8.75 (A&B) (br-s, 1H) |
| a-12 | 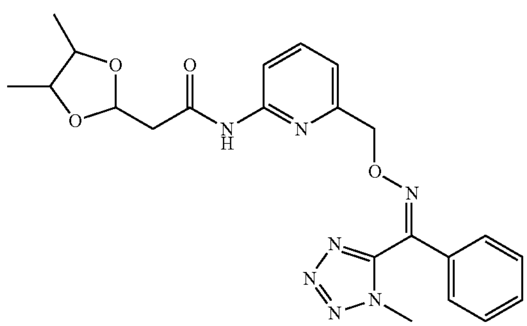 [SMILES: CC1OC(CC(=O)Nc2cccc(CO/N=C(/c3ccccc3)c3nnnn3C)n2)OC1C] | VISC. OIL | A:B = 1:1 diastereomer mixture 1.17-1.35 (A&B) (m, 6H), 2.81 (A&B) (dd, 2H), 3.73 (A&B) (q, 1H), 3.98 (A&B) (s, 3H), 4.23 (A&B) (q, 1H). 5.23 (A) (t, 1H), 5.27 (A&B) (s, 2H), 5.41 (B) (t, 1H), 7.01 (A&B) (d, 1H), 7.35-7.53 (A&B) (m, 5H), 7.70 (A&B) (t, 1H), 8.16 (A&B) (d, 1H), 8.90 (A&B) (br-s, 1H) |
| a-13 | 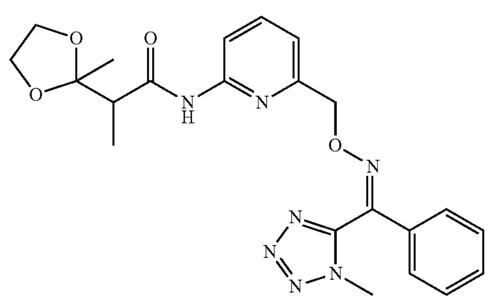 [SMILES: CC(C(=O)Nc1cccc(CO/N=C(/c2ccccc2)c2nnnn2C)n1)C1(C)OCCO1] | VISC. OIL | 1.31 (d, 3H), 1.37 (s, 3H), 2.80 (q, 1H), 3.97-4.16 (m, 4H), 4.01 (s, 3H), 5.28 (s, 2H), 7.00 (d, 1H), 7.34-7.53 (m, 5H), 7.69 (t, 1H), 8.15 (d, 1H), 8.88 (br-s, 1H) |
| a-14 | 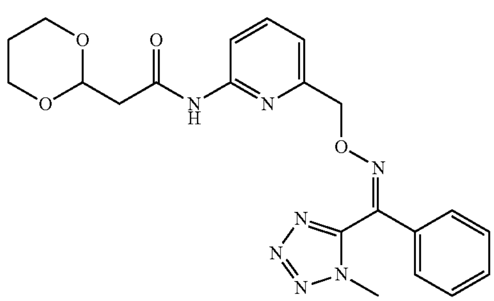 [SMILES: Cn1nnnc1/C(=N\OCc1cccc(NC(=O)CC2OCCCO2)n1)c1ccccc1] | mp 107-108 | — |

TABLE 1-continued

| Compound No. | Chemical structure | Physical property | ¹H-NMR |
|---|---|---|---|
| a-15 | 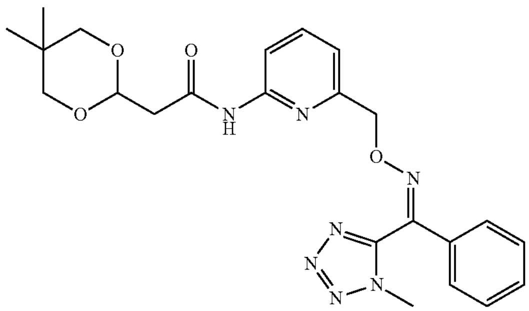 [SMILES: Cn1nnnc1/C(=N\OCc1cccc(NC(=O)CC2OCC(C)(C)CO2)n1)c1ccccc1] | AMR | 0.75 (s, 3H), 0.99 (s, 3H), 2.78 (d, 2H), 3.51 (d, 2H), 3.70 (d, 2H), 3.97 (s, 3H), 4.85 (t, 1H), 5.27 (s, 2H), 7.00 (d, 1H), 7.35-7.53 (m, 5H), 7.68 (t, 1H), 8.14 (d, 1H), 8.86 (br-s, 1H) |
| a-16 | 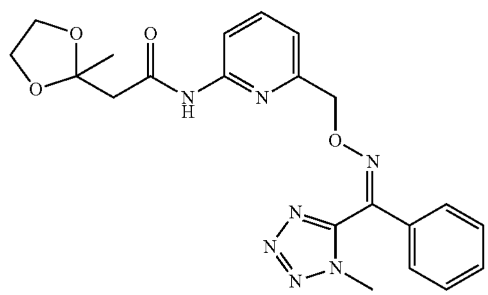 [SMILES: Cn1nnnc1/C(=N\OCc1cccc(NC(=O)CC2(C)OCCO2)n1)c1ccccc1] | VISC. OIL | 1.47 (s, 3H), 2.78 (s, 2H), 4.01 (s, 3H), 4.07 (s, 4H), 5.28 (s, 2H), 7.00 (d, 1H), 7.35-7.53 (m, 5H), 7.69 (t, 1H), 8.13 (d, 1H), 8.80 (br-s, 1H) |
| a-17 | 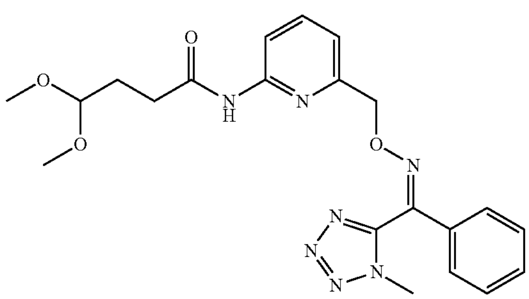 | AMR | 2.04 (dt, 2H), 2.48 (t, 2H), 3.36 (s, 6H), 3.98 (s, 3H), 4.46 (t, 1H), 5.26 (s, 2H), 7.00 (d, 1H), 7.34-7.53 (m, 5H), 7.69 (t, 1H), 8.11 (br-s, 1H), 8.12 (d, 1H) |
| a-18 | 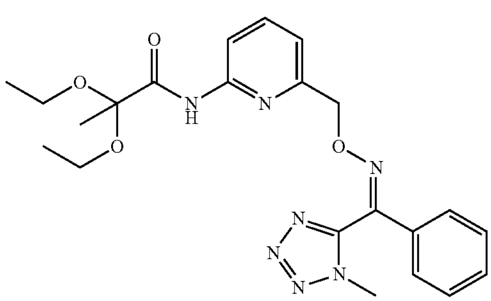 [SMILES: CCOC(C)(OCC)C(=O)Nc1cccc(CO/N=C(/c2ccccc2)c2nnnn2C)n1] | VISC. OIL | 1.26 (t, 6H), 1.58 (s, 3H), 3.49-3.67 (m, 4H), 4.01 (s, 3H), 5.30 (s, 2H), 7.04 (d, 1H), 7.35-7.53 (m, 5H), 7.72 (t, 1H), 8.23 (d, 1H), 9.13 (br-s, 1H) |
| a-19 | 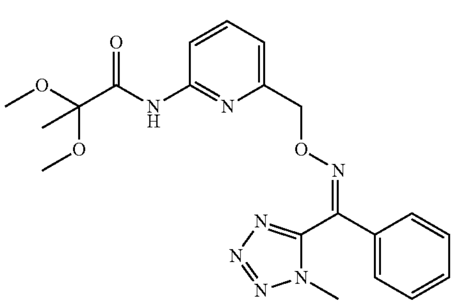 [SMILES: COC(C)(OC)C(=O)Nc1cccc(CO/N=C(/c2ccccc2)c2nnnn2C)n1] | VISC. OIL | 1.57 (s, 3H), 3.23 (s, 6H), 4.00 (s, 3H), 5.30 (s, 2H), 7.05 (d, 1H), 7.35-7.52 (m, 5H), 7.73 (t, 1H), 8.24 (d, 1H), 9.10 (br-s, 1H) |

TABLE 1-continued

| Compound No. | Chemical structure | Physical property | ¹H-NMR |
|---|---|---|---|
| a-20 | 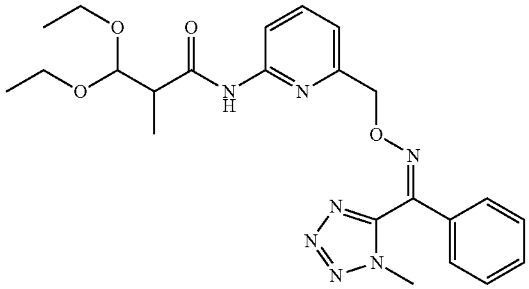 [SMILES: CCOC(OCC)C(C)C(=O)Nc1cccc(CO/N=C(/c2ccccc2)c2nnnn2C)n1] | VISC. OIL | 1.18-1.29 (m, 9H), 2.73 (dq, 1H), 3.53-3.83 (m, 4H), 3.98 (s, 3H), 4.57 (d, 1H), 5.27 (s, 2H), 6.99 (d, 1H), 7.34-7.53 (m, 5H), 7.68 (t, 1H), 8.13 (d, 1H), 8.70 (br-s, 1H) |
| a-21 | 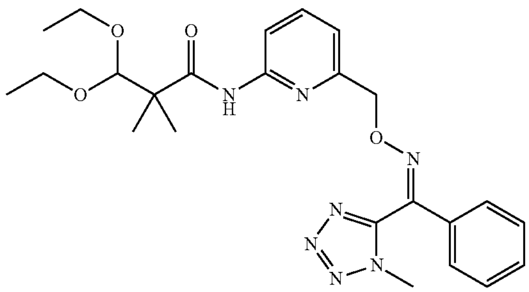 [SMILES: CCOC(OCC)C(C)(C)C(=O)Nc1cccc(CO/N=C(/c2ccccc2)c2nnnn2C)n1] | nD 20.5 1.5410 | — |
| a-22 | 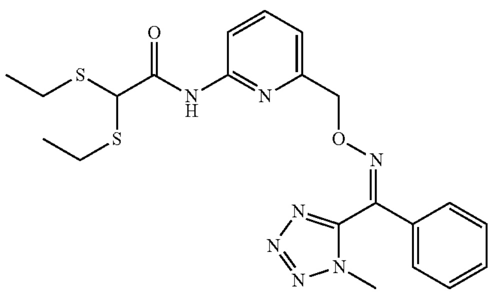 | VISC. OIL | 1.31 (t, 6H), 2.66-2.80 (m, 4H), 4.02 (s, 3H), 4.47 (s, 1H), 5.29 (s, 2H), 7.03 (d, 1H), 7.31-7.52 (m, 5H), 7.71 (t, 1H), 8.10 (d, 1H), 8.88 (br-s, 1H) |
| a-23 | 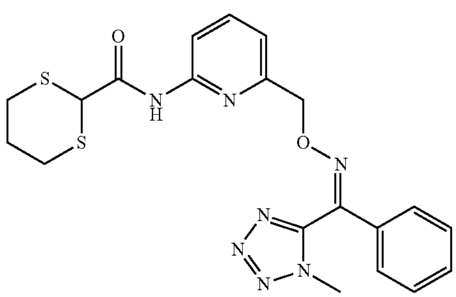 [SMILES: Cn1nnnc1/C(=N\OCc1cccc(NC(=O)C2SCCCS2)n1)c1ccccc1] | AMR | 2.09-2.14 (m, 2H), 2.75-2.81 (m, 2H), 3.13-3.22 (m, 2H), 4.00 (s, 3H), 4.51 (s, 1H), 5.28 (s, 2H), 7.04 (d, 1H), 7.35-7.52 (m, 5H), 7.72 (t, 1H), 8.15 (d, 1H), 8.78 (br-s, 1H) |
| a-24 | 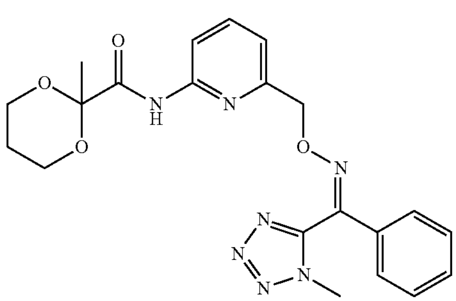 [SMILES: Cn1nnnc1/C(=N\OCc1cccc(NC(=O)C2(C)OCCCO2)n1)c1ccccc1] | AMR | 1.45-1.52 (m, 1H), 1.58 (s, 3H), 2.02-2.08 (m, 1H), 3.87-4.16 (m, 4H), 4.00 (s, 3H), 5.29 (s, 2H), 7.05 (d, 1H), 7.35-7.52 (m, 5H), 7.74 (t, 1H), 8.23 (d, 1H), 8.70 (br-s, 1H) |

TABLE 1-continued

| Compound No. | Chemical structure | Physical property | $^1$H-NMR |
|---|---|---|---|
| a-25 | 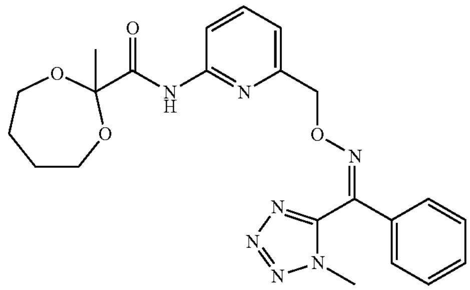 [SMILES: Cn1nnnc1/C(=N\OCc1cccc(NC(=O)C2(C)OCCCCO2)n1)c1ccccc1] | AMR | 1.53 (s, 3H), 1.61-1.74 (m, 4H), 3.69-3.90 (m, 4H), 4.00 (s, 3H), 5.30 (s, 2H), 7.04 (d, 1H), 7.35 (m, 5H), 7.73 (t, 1H), 8.23 (d, 1H), 9.08 (br-s, 1H) |
| a-26 | 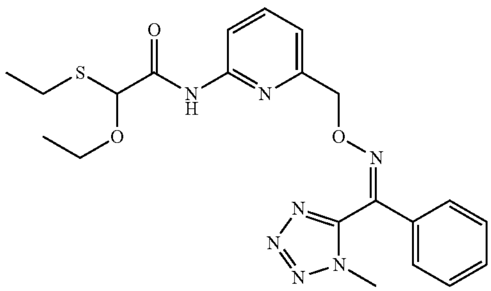 [SMILES: CCOC(SCC)C(=O)Nc1cccc(CO/N=C(/c2ccccc2)c2nnnn2C)n1] | VISC. OIL | 1.26 (t, 3H), 1.35 (t, 3H), 2.66 (q, 2H), 3.57-3,67 (m, 1H), 3.97-4.08 (m, 1H), 4.00 (s, 3H), 4.96 (s, 1H), 5.23 (s, 2H), 7.05 (d, 1H), 7.34-7.52 (m, 5H), 7.73 (t, 1H), 8.21 (d, 1H), 8.84 (br-s, 1H) |
| a-27 | 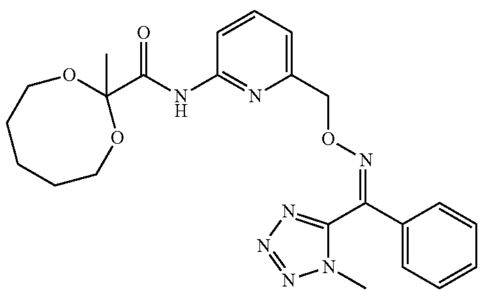 [SMILES: Cn1nnnc1/C(=N\OCc1cccc(NC(=O)C2(C)OCCCCCO2)n1)c1ccccc1] | VISC. OIL | 1.58 (s, 3H), 1.59-1.77 (m, 6H), 3.67-3.95 (m, 4H), 4.00 (s, 3H), 5.30 (s, 2H), 7.06 (d, 1H), 7.35-7.52 (m, 5H), 7.73 (t, 1H), 8.24 (d, 1H), 9.11 (br-s, 1H) |
| a-28 | 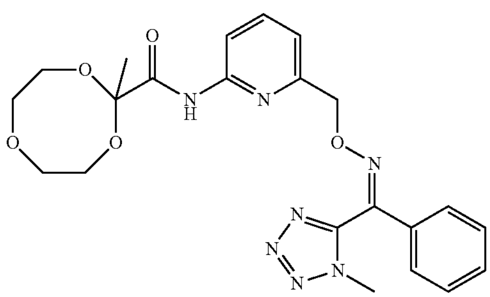 [SMILES: Cn1nnnc1/C(=N\OCc1cccc(NC(=O)C2(C)OCCOCCO2)n1)c1ccccc1] | VISC. OIL | 1.63 (s, 3H), 3.78-3.96 (m, 8H), 4.00 (s, 3H), 5.30 (s, 2H), 7.05 (d, 1H), 7.35-7.53 (m, 5H), 7.73 (t, 1H), 8.21 (d, 1H), 9.11 (br-s, 1H) |
| a-29 | 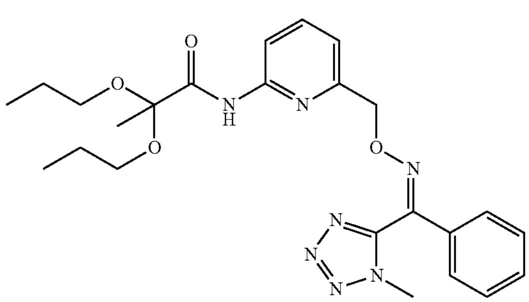 [SMILES: CCCOC(C)(OCCC)C(=O)Nc1cccc(CO/N=C(/c2ccccc2)c2nnnn2C)n1] | nD 20.7 1.5411 | — |

TABLE 1-continued

| Compound No. | Chemical structure | Physical property | ¹H-NMR |
|---|---|---|---|
| a-30 | 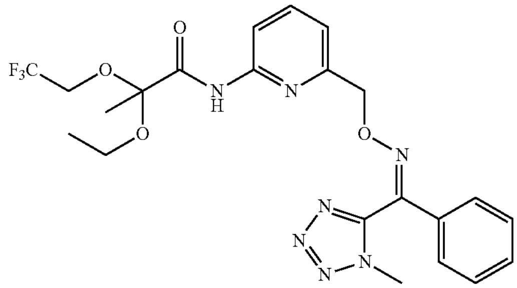 [SMILES: CCOC(C)(OCC(F)(F)F)C(=O)Nc1cccc(CO/N=C(/c2ccccc2)c2nnnn2C)n1] | VISC. OIL | 1.30 (t, 3H), 1.64 (s, 3H), 3.63-3.70 (m, 2H), 3.92 (q, 2H), 4.02 (s, 3H), 5.30 (s, 2H), 7.06 (d, 1H), 7.34-7.52 (m, 5H), 7.73 (t, 1H), 8.19 (d, 1H), 8.96 (br-s, 1H) |
| a-31 | 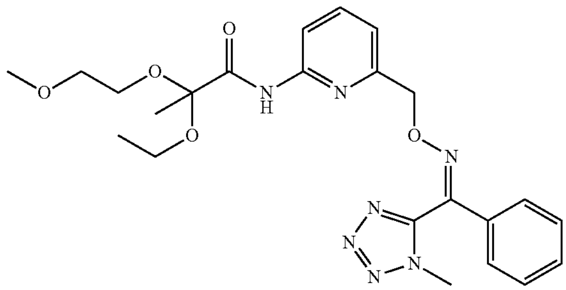 [SMILES: CCOC(C)(OCCOC)C(=O)Nc1cccc(CO/N=C(/c2ccccc2)c2nnnn2C)n1] | nD 20.2 1.5450 | — |
| a-32 | 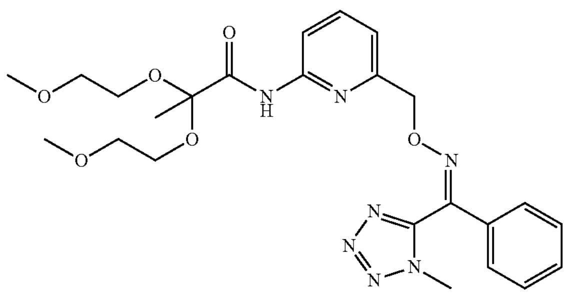 [SMILES: COCCOC(C)(OCCOC)C(=O)Nc1cccc(CO/N=C(/c2ccccc2)c2nnnn2C)n1] | nD 20.4 1.5475 | — |
| a-33 | HCl | mp 70-73 | — |
| a-34 | 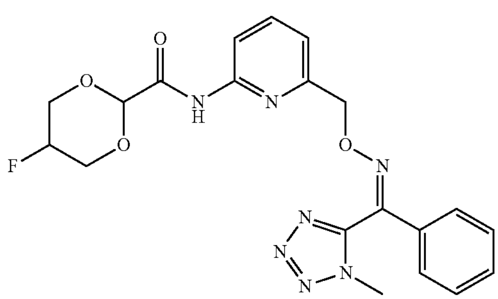 [SMILES: Cn1nnnc1/C(=N\OCc1cccc(NC(=O)C2OCC(F)CO2)n1)c1ccccc1] | | |

TABLE 1-continued

| Compound No. | Chemical structure | Physical property | ¹H-NMR |
| --- | --- | --- | --- |
| a-35 | 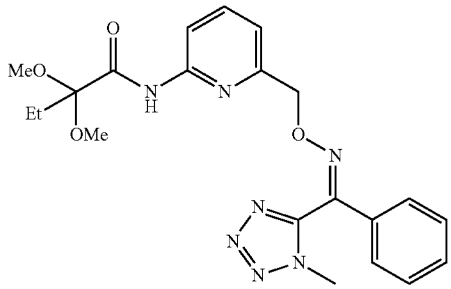 [SMILES: CCC(OC)(OC)C(=O)Nc1cccc(CO/N=C(/c2ccccc2)c2nnnn2C)n1] | | |
| a-36 | 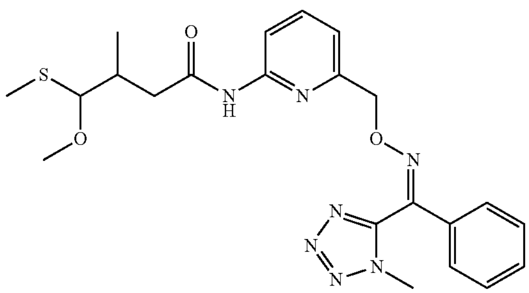 [SMILES: COC(SC)C(C)CC(=O)Nc1cccc(CO/N=C(/c2ccccc2)c2nnnn2C)n1] | | |
| a-37 | 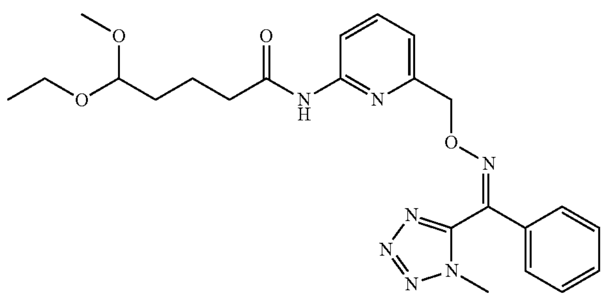 [SMILES: CCOC(CCCC(=O)Nc1cccc(CO/N=C(/c2ccccc2)c2nnnn2C)n1)OC] | | |
| a-38 | 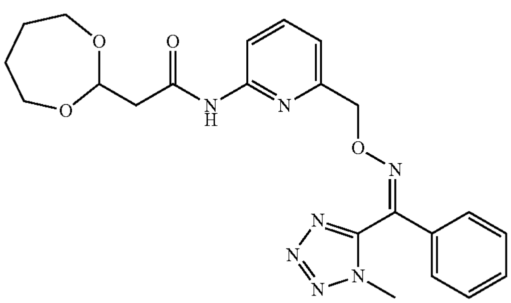 [SMILES: Cn1nnnc1/C(=N\OCc1cccc(NC(=O)CC2OCCCCO2)n1)c1ccccc1] | | |
| a-39 | 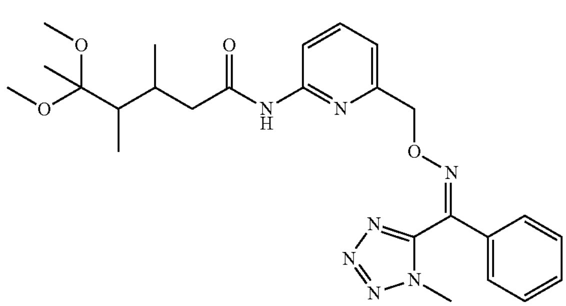 | | |

TABLE 1-continued

| Compound No. | Chemical structure | Physical property | ¹H-NMR |
|---|---|---|---|
| a-40 | 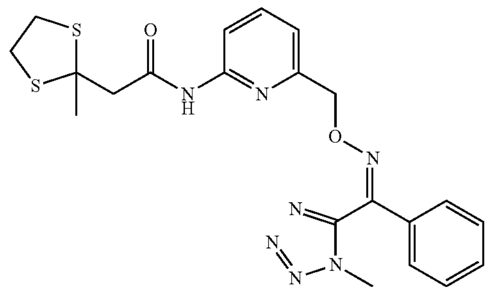 [SMILES: CN(N=N)C(=N)/C(=N\OCc1cccc(NC(=O)CC2(C)SCCS2)n1)c1ccccc1] | | |
| a-41 | 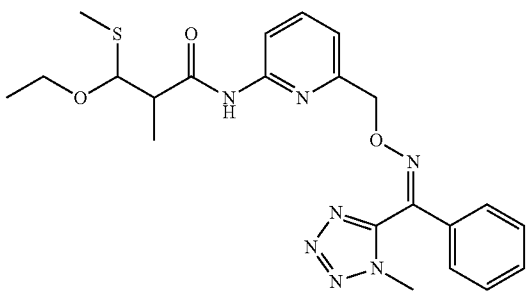 [SMILES: CCOC(SC)C(C)C(=O)Nc1cccc(CO/N=C(/c2ccccc2)c2nnnn2C)n1] | | |
| a-42 | 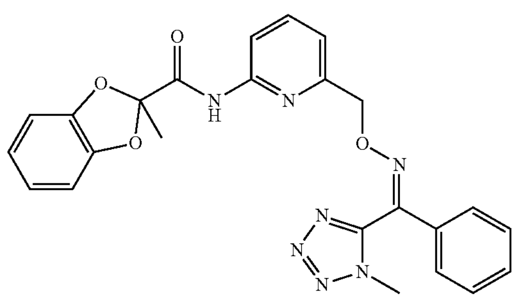 [SMILES: Cn1nnnc1/C(=N\OCc1cccc(NC(=O)C2(C)Oc3ccccc3O2)n1)c1ccccc1] | | |
| a-43 | 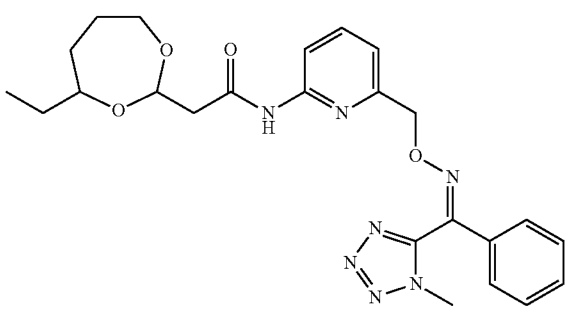 [SMILES: CCC1CCCOC(CC(=O)Nc2cccc(CO/N=C(/c3ccccc3)c3nnnn3C)n2)O1] | | |
| a-44 | 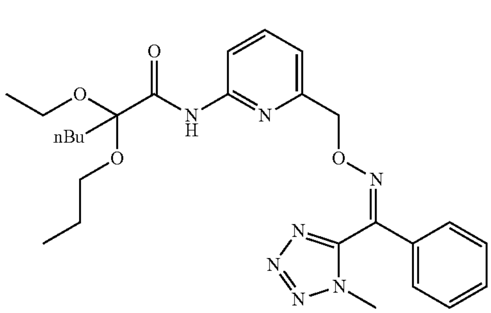 | | |

TABLE 1-continued

| Compound No. | Chemical structure | Physical property | ¹H-NMR |
|---|---|---|---|
| a-45 | 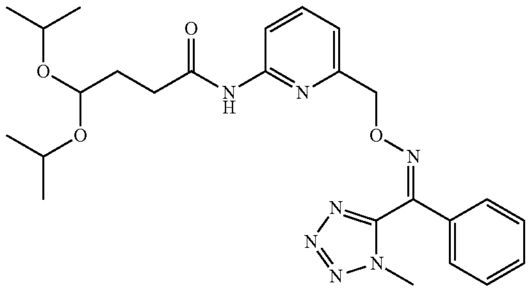 [SMILES: CC(C)OC(CCC(=O)Nc1cccc(CO/N=C(/c2ccccc2)c2nnnn2C)n1)OC(C)C] | | |
| a-46 | 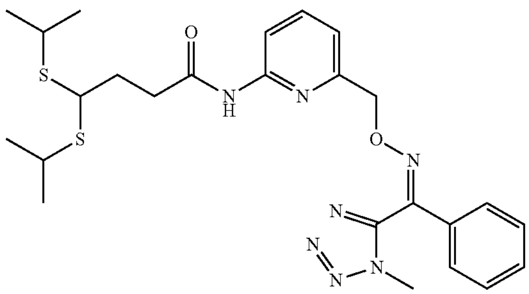 [SMILES: CC(C)SC(CCC(=O)Nc1cccc(CO/N=C(\C(=N)N(C)N=N)c2ccccc2)n1)SC(C)C] | | |
| a-47 | 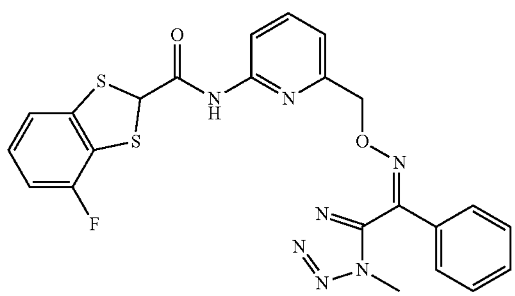 [SMILES: CN(N=N)C(=N)/C(=N\OCc1cccc(NC(=O)C2Sc3cccc(F)c3S2)n1)c1ccccc1] | | |
| a-48 | 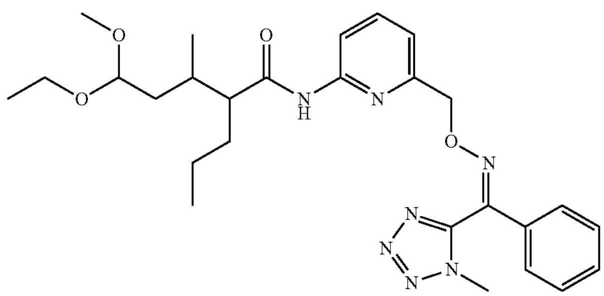 [SMILES: CCCC(C(=O)Nc1cccc(CO/N=C(/c2ccccc2)c2nnnn2C)n1)C(C)CC(OC)OCC] | | |
| a-49 | 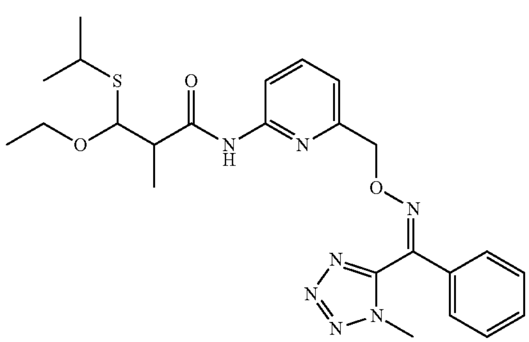 [SMILES: CCOC(SC(C)C)C(C)C(=O)Nc1cccc(CO/N=C(/c2ccccc2)c2nnnn2C)n1] | | |

TABLE 1-continued

| Compound No. | Chemical structure | Physical property | ¹H-NMR |
|---|---|---|---|
| a-50 | 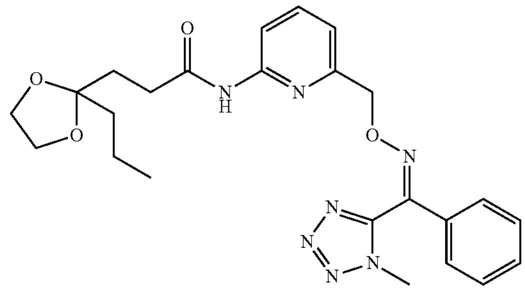 [SMILES: CCCC1(CCC(=O)Nc2cccc(CO/N=C(/c3ccccc3)c3nnnn3C)n2)OCCO1] | | |
| a-51 | 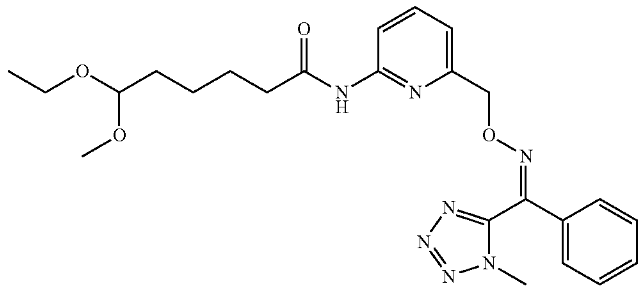 | | |
| a-52 | 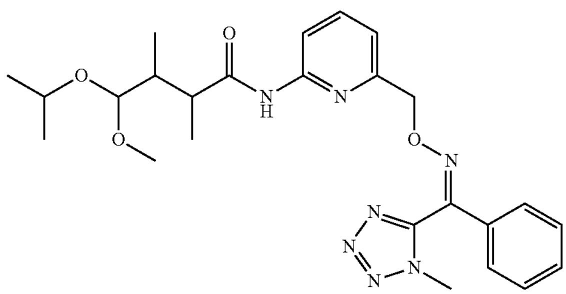 [SMILES: COC(OC(C)C)C(C)C(C)C(=O)Nc1cccc(CO/N=C(/c2ccccc2)c2nnnn2C)n1] | | |
| a-53 | 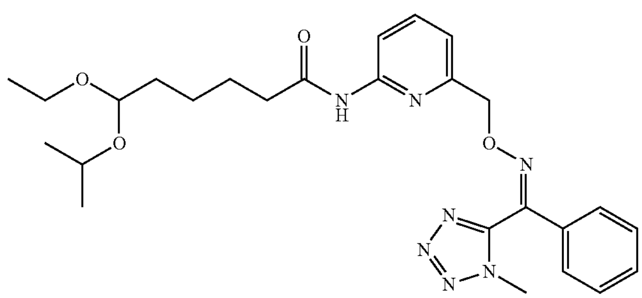 [SMILES: CCOC(CCCCC(=O)Nc1cccc(CO/N=C(/c2ccccc2)c2nnnn2C)n1)OC(C)C] | | |
| a-54 | 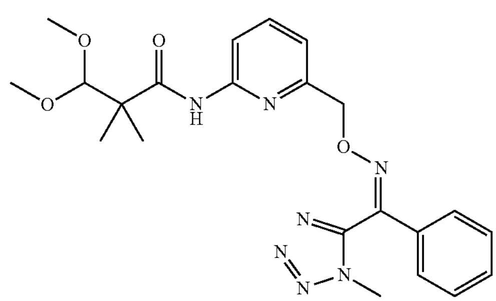 [SMILES: COC(OC)C(C)(C)C(=O)Nc1cccc(CO/N=C(\C(=N)N(C)N=N)c2ccccc2)n1] | | |

TABLE 1-continued

| Compound No. | Chemical structure | Physical property | ¹H-NMR |
|---|---|---|---|
| a-55 | 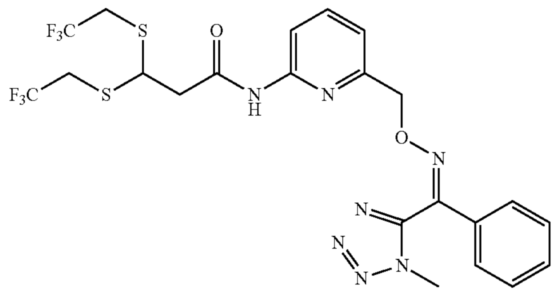 [SMILES: CN(N=N)C(=N)/C(=N\OCc1cccc(NC(=O)CC(SCC(F)(F)F)SCC(F)(F)F)n1)c1ccccc1] | | |
| a-56 | 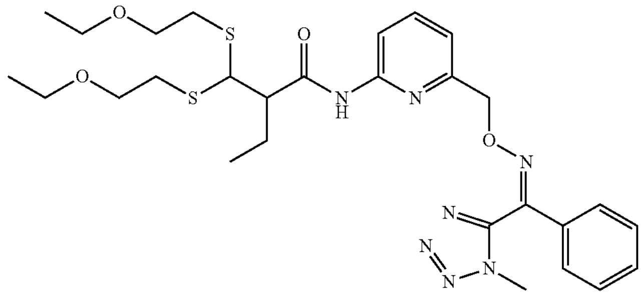 [SMILES: CCOCCSC(SCCOCC)C(CC)C(=O)Nc1cccc(CO/N=C(\C(=N)N(C)N=N)c2ccccc2)n1] | | |

TABLE 2

| Compound No. | Chemical structure | Physical property | ¹H-NMR |
|---|---|---|---|
| b-1 | 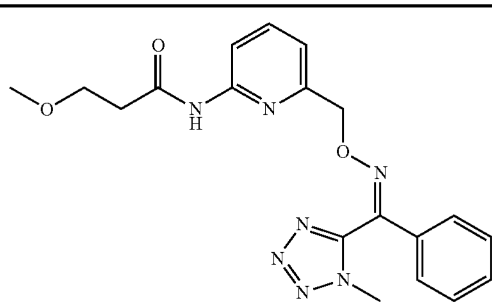 | nD20.4 1.5733 | — |
| b-2 | 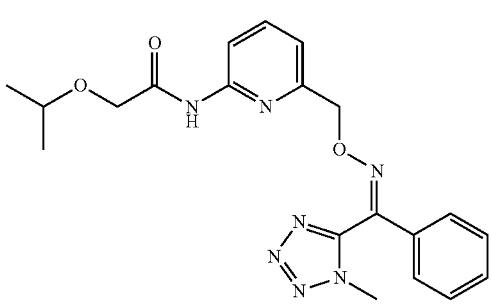 [SMILES: CC(C)OCC(=O)Nc1cccc(CO/N=C(/c2ccccc2)c2nnnn2C)n1] | VISC. OIL | 1.27 (d, 6H), 3.75 (sev, 1H), 4.01 (s, 3H), 4.07 (s, 2H), 5.30 (s, 2H), 7.03 (d, 1H), 7.34-7.52 (m, 5H), 7.70 (t, 1H), 8.17 (d, 1H), 8.88 (br-s, 1H). |

TABLE 2-continued

| Compound No. | Chemical structure | Physical property | $^1$H-NMR |
|---|---|---|---|
| b-3 | 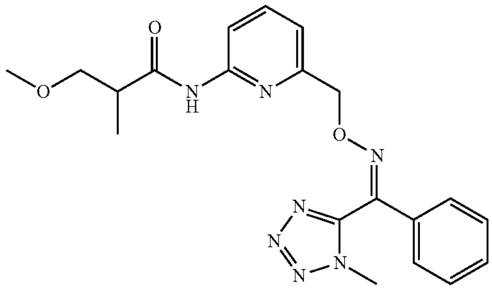 [SMILES: COCC(C)C(=O)Nc1cccc(CO/N=C(/c2ccccc2)c2nnnn2C)n1] | mp 66-68 | — |
| b-4 | 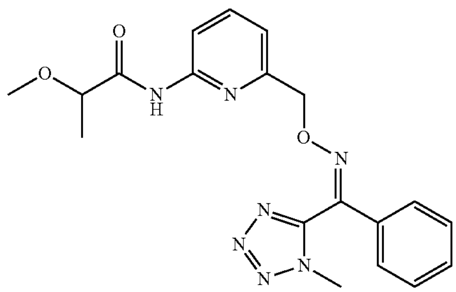 [SMILES: COC(C)C(=O)Nc1cccc(CO/N=C(/c2ccccc2)c2nnnn2C)n1] | VISC. OIL | 1.12 (d, 3H), 3.14 (s, 3H), 3.54 (q, 1H), 3.65 (s, 3H), 4.94 (s, 2H), 6.69 (d, 1H), 7.04-7.18 (m, 5H), 7.37 (t, 1H), 7.84 (d, 1H), 8.53 (s, 1H). |
| b-5 | 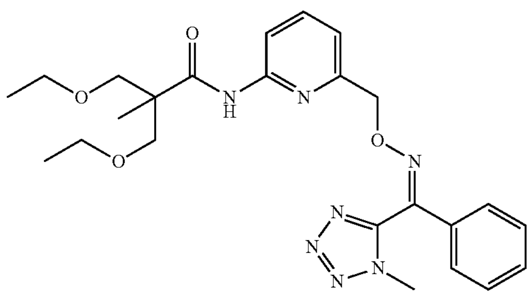 [SMILES: CCOCC(C)(COCC)C(=O)Nc1cccc(CO/N=C(/c2ccccc2)c2nnnn2C)n1] | VISC. OIL | 1.25 (t, 6H), 1.26 (s, 3H), 3.58 (q, 4H), 3.61 (d, 2H), 3.64 (d, 2H), 3.98 (s, 2H), 5.27 (s, 2H), 6.97 (d, 1H), 7.34-7.53 (m, 5H), 7.66 (dd, 1H), 8.14 (d, 1H), 9.79 (s, 1H) |
| b-6 | 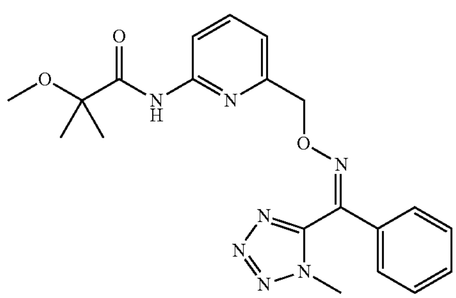 [SMILES: COC(C)(C)C(=O)Nc1cccc(CO/N=C(/c2ccccc2)c2nnnn2C)n1] | mp 104-105 | — |
| b-7 | 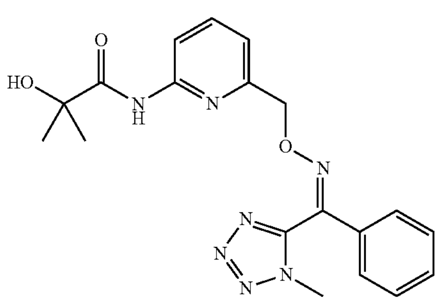 [SMILES: Cn1nnnc1/C(=N\OCc1cccc(NC(=O)C(C)(C)O)n1)c1ccccc1] | mp 144-146 | — |

TABLE 2-continued

| Compound No. | Chemical structure | Physical property | ¹H-NMR |
|---|---|---|---|
| b-8 | 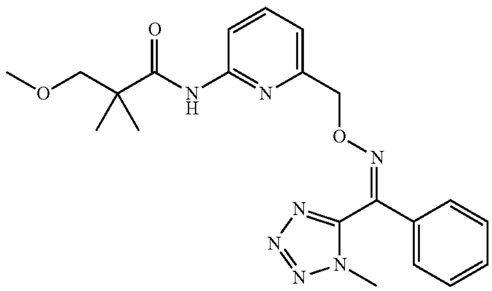 [SMILES: COCC(C)(C)C(=O)Nc1cccc(CO/N=C(/c2ccccc2)c2nnnn2C)n1] | mp 60-61 | — |
| b-9 | 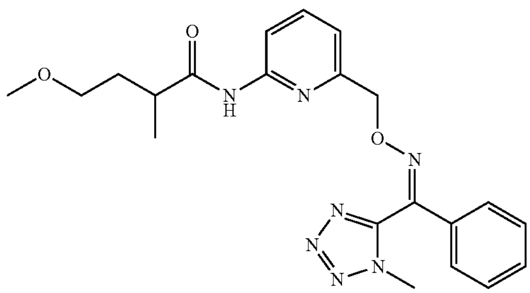 [SMILES: COCCC(C)C(=O)Nc1cccc(CO/N=C(/c2ccccc2)c2nnnn2C)n1] | AMR | 1.26 (d, 3H), 1.73-1.98 (m, 2H), 2.62-2.65 (m, 1H), 3.34 (s, 3H), 3.43-3.47 (m, 3H), 3.98 (s, 3H), 5.27 (s, 2H), 7.00 (d, 1H), 7.35-7.52 (m, 5H), 7.71 (t, 1H), 8.16 (d, 1H). |
| b-10 | 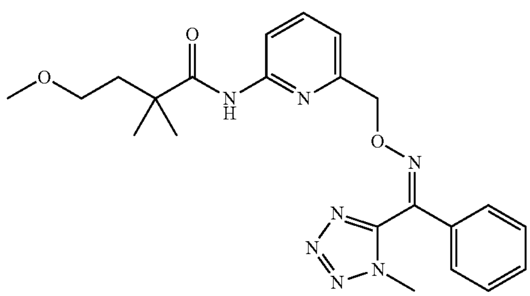 [SMILES: COCCC(C)(C)C(=O)Nc1cccc(CO/N=C(/c2ccccc2)c2nnnn2C)n1] | mp 86-87 | — |
| b-11 | 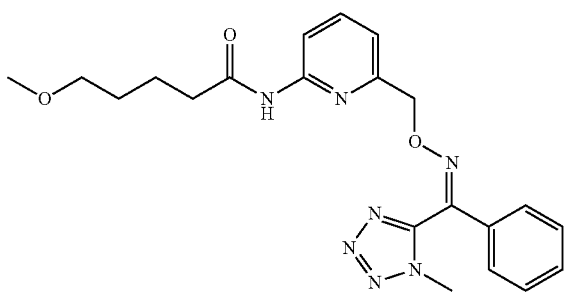 | VISC. OIL | 1.67-1.86 (m, 4H), 2.22-2.49 (m, 2H), 3.33 (s, 3H), 3.42 (t, 2H), 3.97 (s, 3H), 5.25 (s, 2H), 7.01 (d, 1H), 7.34-7.51 (m, 5H), 7.73 (t, 1H), 8.20 (d, 1H), 8.96 (s, 1H). |
| b-12 | 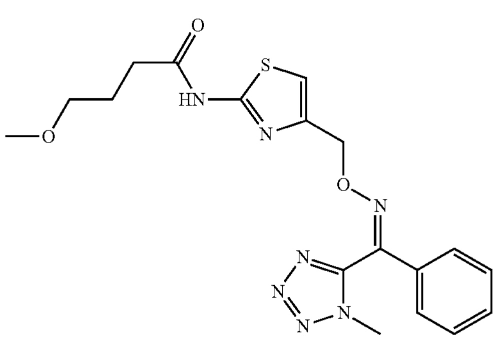 [SMILES: COCCCC(=O)Nc1nc(CO/N=C(/c2ccccc2)c2nnnn2C)cs1] | AMR | 1.92-2.05 (m, 2H), 2.56 (t, 2H), 3.40 (s, 3H), 3.50 (t, 3H), 3.95 (s, 3H), 5.25 (s, 2H), 6.90 (s, 1H), 7.35-7.54 (m, 5H), 9.56 (br-s, 1H) |

TABLE 2-continued

| Compound No. | Chemical structure | Physical property | ¹H-NMR |
|---|---|---|---|
| b-13 | 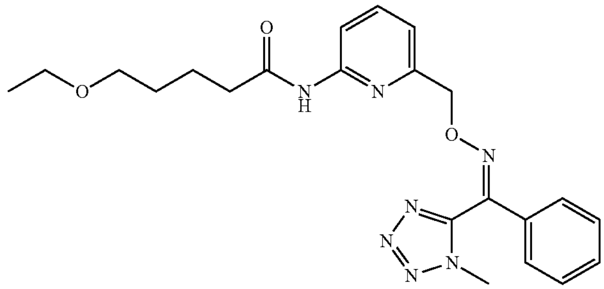 [SMILES: CCOCCCCC(=O)Nc1cccc(CO/N=C(/c2ccccc2)c2nnnn2C)n1] | | |
| b-14 | 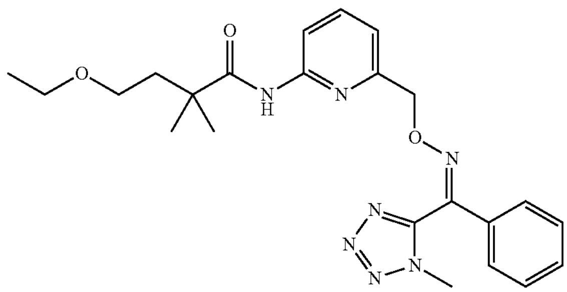 [SMILES: CCOCCC(C)(C)C(=O)Nc1cccc(CO/N=C(/c2ccccc2)c2nnnn2C)n1] | | |
| b-15 | 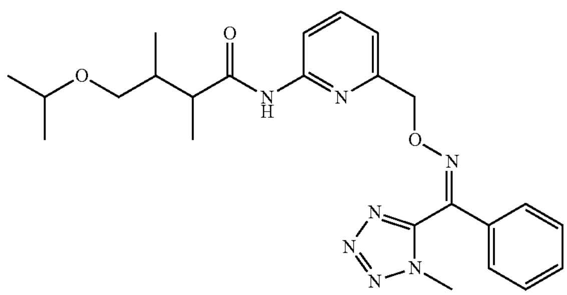 [SMILES: CC(C)OCC(C)C(C)C(=O)Nc1cccc(CO/N=C(/c2ccccc2)c2nnnn2C)n1] | | |
| b-16 | 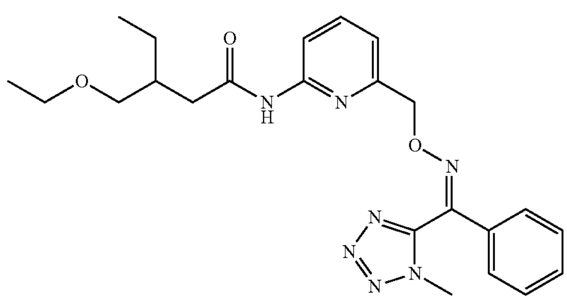 [SMILES: CCOCC(CC)CC(=O)Nc1cccc(CO/N=C(/c2ccccc2)c2nnnn2C)n1] | | |
| b-17 | 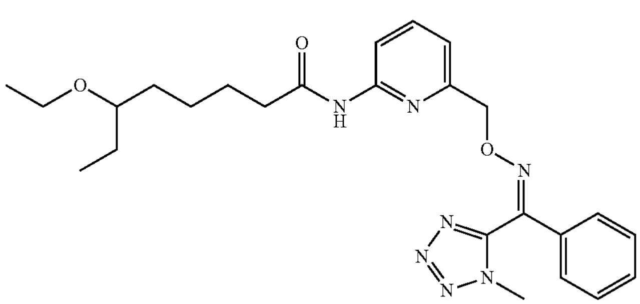 [SMILES: CCOC(CC)CCCCC(=O)Nc1cccc(CO/N=C(/c2ccccc2)c2nnnn2C)n1] | | |

TABLE 2-continued

| Compound No. | Chemical structure | Physical property | $^1$H-NMR |
|---|---|---|---|
| b-18 | 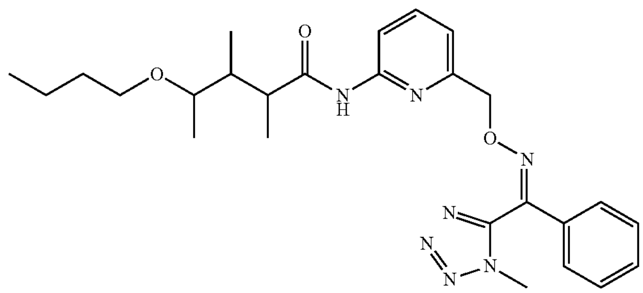 [SMILES: CCCCOC(C)C(C)C(C)C(=O)Nc1cccc(CO/N=C(\C(=N)N(C)N=N)c2ccccc2)n1] | | |
| b-19 | 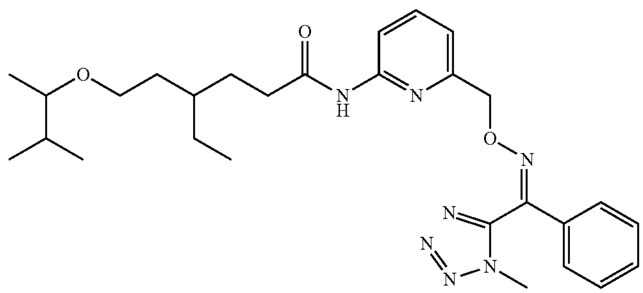 [SMILES: CCC(CCOC(C)C(C)C)CCC(=O)Nc1cccc(CO/N=C(\C(=N)N(C)N=N)c2ccccc2)n1] | | |
| b-20 | 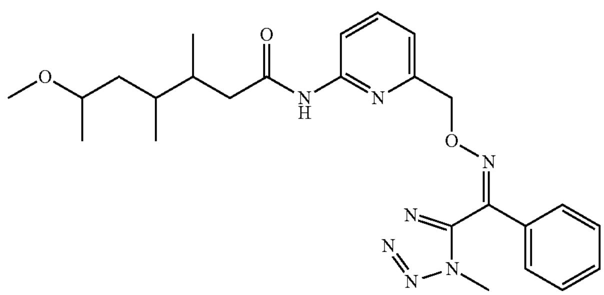 [SMILES: COC(C)CC(C)C(C)CC(=O)Nc1cccc(CO/N=C(\C(=N)N(C)N=N)c2ccccc2)n1] | | |
| b-21 | 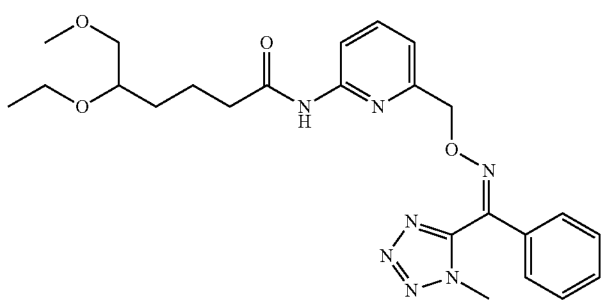 [SMILES: CCOC(CCCC(=O)Nc1cccc(CO/N=C(/c2ccccc2)c2nnnn2C)n1)COC] | | |
| b-22 | 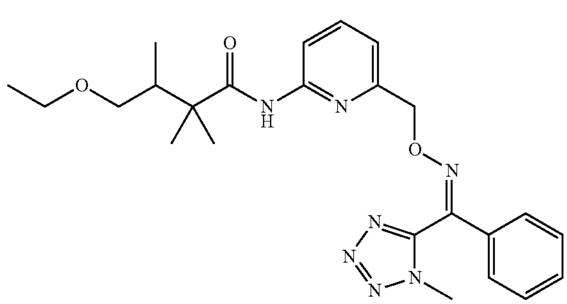 [SMILES: CCOCC(C)C(C)(C)C(=O)Nc1cccc(CO/N=C(/c2ccccc2)c2nnnn2C)n1] | | |

TABLE 2-continued

| Compound No. | Chemical structure | Physical property $^1$H-NMR |
|---|---|---|
| b-23 | 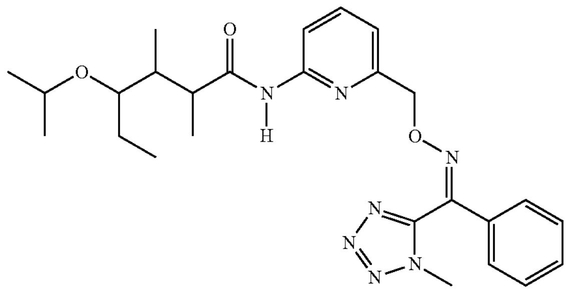 | |
| b-24 | 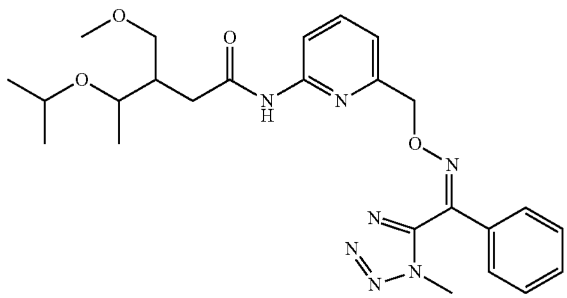 [SMILES: COCC(CC(=O)Nc1cccc(CO/N=C(\C(=N)N(C)N=N)c2ccccc2)n1)C(C)OC(C)C] | |
| b-25 | 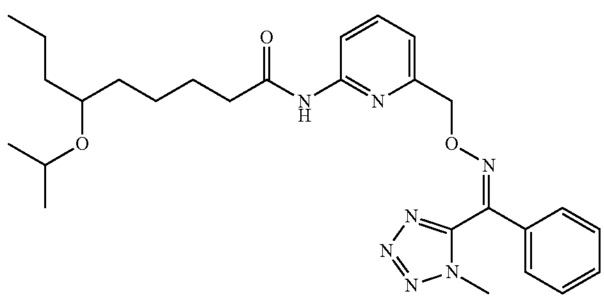 [SMILES: CCCC(CCCCC(=O)Nc1cccc(CO/N=C(/c2ccccc2)c2nnnn2C)n1)OC(C)C] | |
| b-26 | 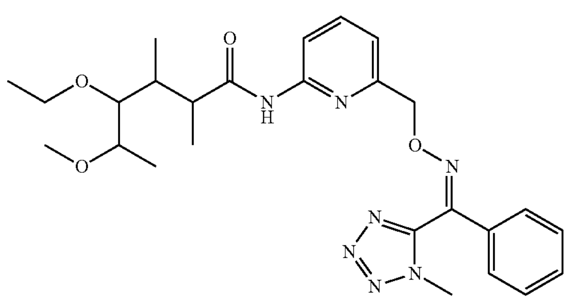 [SMILES: CCOC(C(C)OC)C(C)C(C)C(=O)Nc1cccc(CO/N=C(/c2ccccc2)c2nnnn2C)n1] | |
| b-27 | 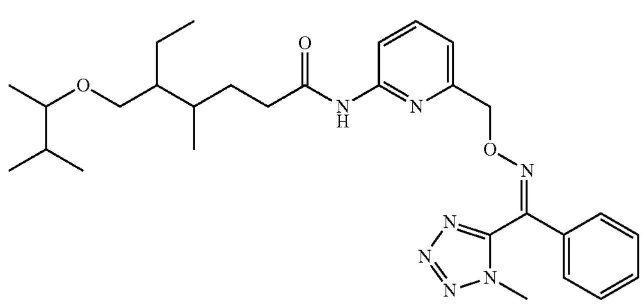 [SMILES: CCC(COC(C)C(C)C)C(C)CCC(=O)Nc1cccc(CO/N=C(/c2ccccc2)c2nnnn2C)n1] | |

TABLE 2-continued

| Compound No. | Chemical structure | Physical property $^1$H-NMR |
|---|---|---|
| b-28 | 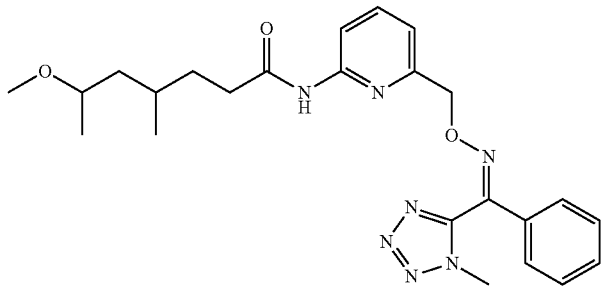 [SMILES: COC(C)CC(C)CCC(=O)Nc1cccc(CO/N=C(/c2ccccc2)c2nnnn2C)n1] | |
| b-29 | 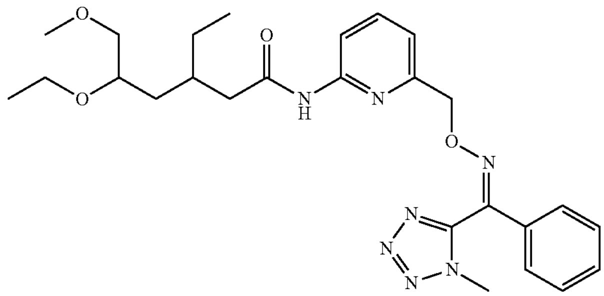 [SMILES: CCOC(COC)CC(CC)CC(=O)Nc1cccc(CO/N=C(/c2ccccc2)c2nnnn2C)n1] | |
| b-30 | 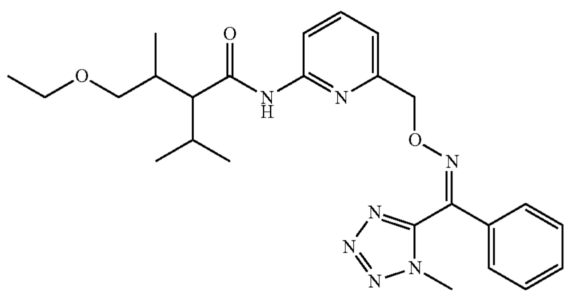 [SMILES: CCOCC(C)C(C(=O)Nc1cccc(CO/N=C(/c2ccccc2)c2nnnn2C)n1)C(C)C] | |
| b-31 | 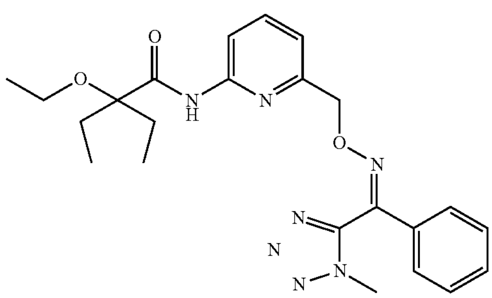 | |
| b-32 | 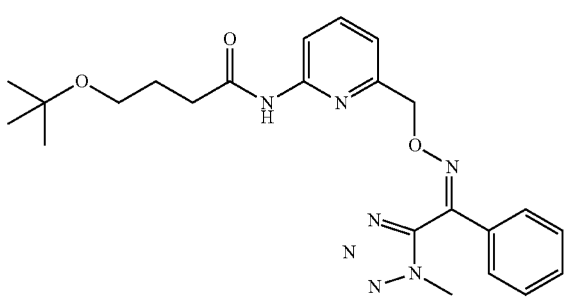 | |

TABLE 3

| Compound No. | Chemical structure | Physical property | ¹H-NMR |
|---|---|---|---|
| c-1 | 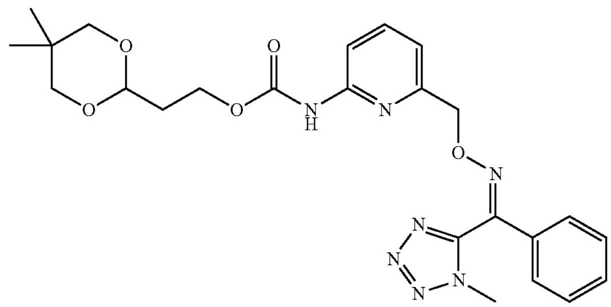 [SMILES: Cn1nnnc1/C(=N\OCc1cccc(NC(=O)OCCC2OCC(C)(C)CO2)n1)c1ccccc1] | AMR | 0.73 (s, 3H), 1.19 (s, 3H), 2.03 (dt, 2H), 3.42 (d, 2H), 3.61 (d, 2H), 3.98 (s, 3H), 4.33 (t, 2H), 4.58 (t, 1H), 5.26 (s, 2H), 6.96 (d, 1H), 7.32-7.53 (m, 6H), 7.68 (t, 1H), 7.90 (d, 1H) |
| c-2 | 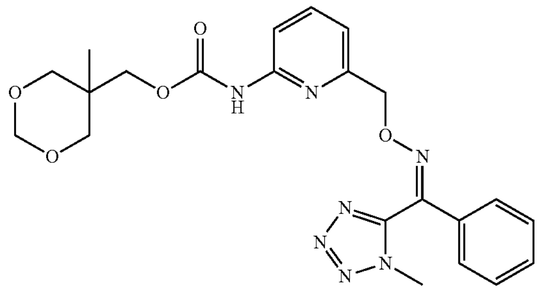 [SMILES: Cn1nnnc1/C(=N\OCc1cccc(NC(=O)OCC2(C)COCOC2)n1)c1ccccc1] | AMR | 0.88 (s, 3H), 3.47 (d, 2H), 3.86 (d, 2H), 3.97 (s, 3H), 4.34 (s, 2H), 4.68 (d, 1H), 4.98 (d, 1H), 5.26 (s, 2H), 6.97 (d, 1H), 7.35-7.53 (m, 6H), 7.69 (t, 1H), 7.90 (d, 1H) |
| c-3 | 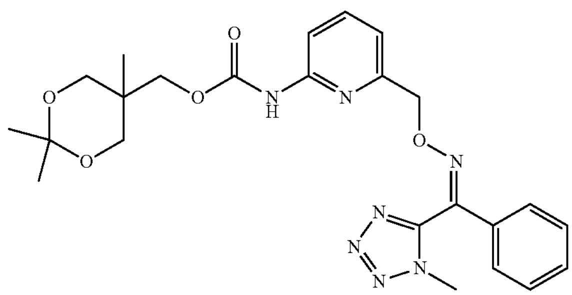 [SMILES: Cn1nnnc1/C(=N\OCc1cccc(NC(=O)OCC2(C)COC(C)(C)OC2)n1)c1ccccc1] | VISC. OIL | 0.89 (s, 3H), 1.41 (s, 3H), 1.45 (s, 3H), 3.64 (d, 2H), 3.69 (d, 2H), 3.97 (s, 3H), 4.30 (s, 2H), 5.26 (s, 2H), 6.97 (d, 1H), 7.34-7.52 (m, 6H), 7.69 (t, 1H), 7.90 (d, 1H) |
| c-4 | 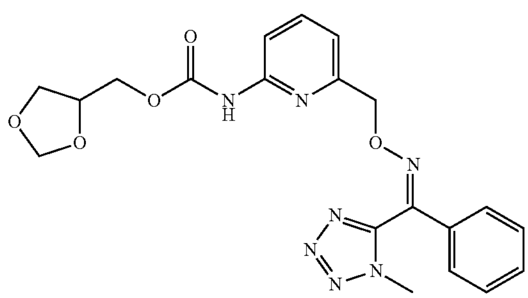 [SMILES: Cn1nnnc1/C(=N\OCc1cccc(NC(=O)OCC2COCO2)n1)c1ccccc1] | mp 104-105 | — |
| c-5 | 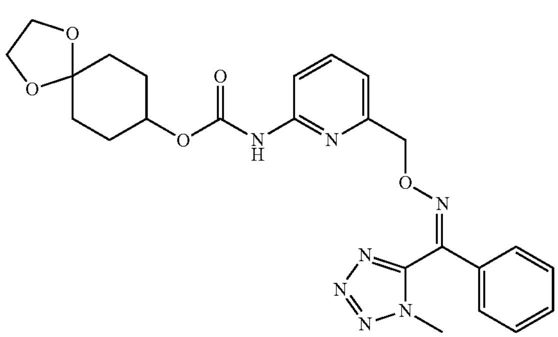 [SMILES: Cn1nnnc1/C(=N\OCc1cccc(NC(=O)OC2CCC3(CC2)OCCO3)n1)c1ccccc1] | AMR | 1.65-1.98 (m, 8H), 3.93-4.00 (m, 4H), 3.98 (s, 3H), 4.90 (tt, 1H), 5.26 (s, 2H), 6.95 (d, 1H), 7.31-7.53 (m, 6H), 7.68 (t, 1H), 7.88 (d, 1H) |

TABLE 3-continued

| Compound No. | Chemical structure | Physical property | ¹H-NMR |
|---|---|---|---|
| c-6 | 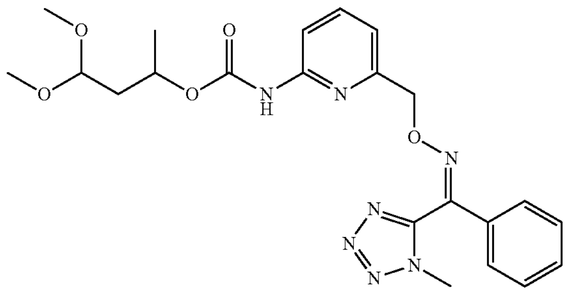 [SMILES: COC(CC(C)OC(=O)Nc1cccc(CO/N=C(/c2ccccc2)c2nnnn2C)n1)OC] | VISC. OIL | 1.33 (d, 3H), 1.78-2.04 (m, 2H), 3.32 (s, 3H), 3.34 (s, 3H), 3.98 (s, 3H), 4.48-4.52 (m, 1H), 5.01-5.08 (m, 1H), 5.25 (s, 2H), 6.95 (d, 1H), 7.23-7.52 (m, 6H), 7.67 (t, 1H), 7.89 (d, 1H) |
| c-7 | 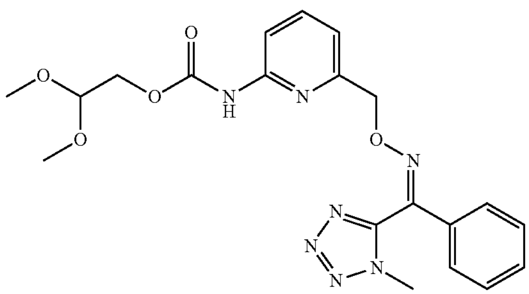 [SMILES: COC(COC(=O)Nc1cccc(CO/N=C(/c2ccccc2)c2nnnn2C)n1)OC] | VISC. OIL | 3.40 (s, 6H), 3.98 (s, 3H), 4.21 (d, 2H), 4.62 (t, 1H), 5.26 (s, 2H), 6.97 (d, 1H), 7.35-7.53 (m, 6H), 7.69 (t, 1H), 7.88 (d, 1H) |
| c-8 | 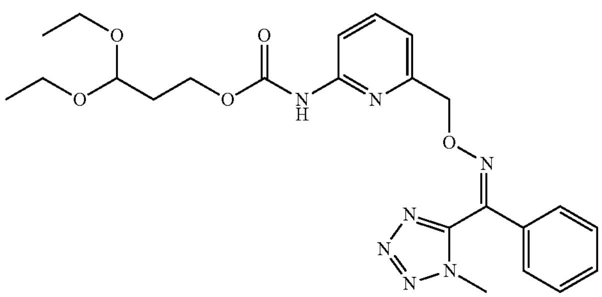 [SMILES: CCOC(CCOC(=O)Nc1cccc(CO/N=C(/c2ccccc2)c2nnnn2C)n1)OCC] | VISC. OIL | 1.21 (t, 6H), 2.00 (dt, 2H), 3.47-3.73 (m, 4H), 3.98 (s, 3H), 4.28 (t, 2H), 4.65 (t, 1H), 5.26 (s, 2H), 6.96 (d, 1H), 7.33-7.53 (m, 6H), 7.68 (t, 1H), 7.89 (d, 1H) |
| c-9 | 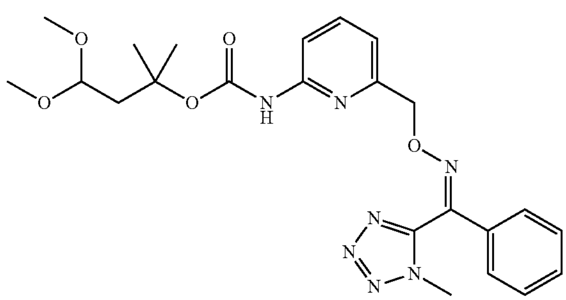 [SMILES: COC(CC(C)(C)OC(=O)Nc1cccc(CO/N=C(/c2ccccc2)c2nnnn2C)n1)OC] | VISC. OIL | 1.55 (s, 6H), 2.17 (d, 2H), 3.31 (s, 6H), 3.97 (s, 3H), 4.56 (t, 1H), 5.26 (s, 2H), 6.93 (d, 1H), 7.34-7.52 (m, 6H), 7.66 (t, 1H), 7.86 (d, 1H) |
| c-10 | 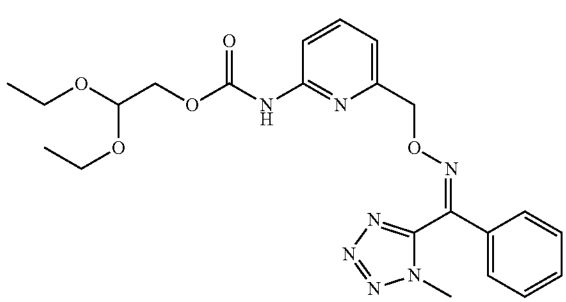 [SMILES: CCOC(COC(=O)Nc1cccc(CO/N=C(/c2ccccc2)c2nnnn2C)n1)OCC] | VISC. OIL | 1.24 (t, 6H), 3.54-3.79 (m, 4H), 3.98 (s, 3H), 4.20 (d, 2H), 4.73 (t, 1H), 5.26 (s, 2H), 6.97 (d, 1H), 7.34-7.53 (m, 6H), 7.68 (t, 1H), 7.89 (d, 1H) |

TABLE 3-continued

| Compound No. | Chemical structure | Physical property $^1$H-NMR |
|---|---|---|
| c-11 | | VISC. OIL | 1.24-1.62 (m, 2H), 1.31 (d, 3H), 2.04-2.18 (m, 1H), 3.74-3.83 (m, 2H), 3.98 (s, 3H), 4.13-4.18 (m, 2H), 4.61 (d, 1H), 4.90-4.98 (m, 1H), 5.25 (s, 2H), 6.95 (d, 1H), 7.30-7.52 (m, 6H), 7.67 (t, 1H), 7.90 (d, 1H) |
| c-12 | 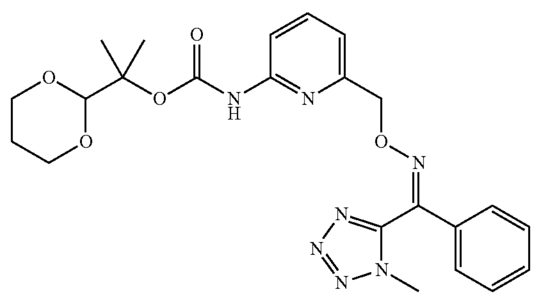 [SMILES: Cn1nnnc1/C(=N\OCc1cccc(NC(=O)OC(C)(C)C2OCCCO2)n1)c1ccccc1] | AMR 1.28-1.38 (m, 2H), 1.51 (s, 6H), 2.05-2.10 (m, 1H), 3.76-3.85 (m, 2H), 3.97 (s, 3H), 4.09-4.17 (m, 2H), 4.93 (s, 1H), 5.24 (s, 2H), 6.92 (d, 1H), 7.30-7.53 (m, 6H), 7.65 (t, 1H), 7.83 (d, 1H) |
| c-13 | 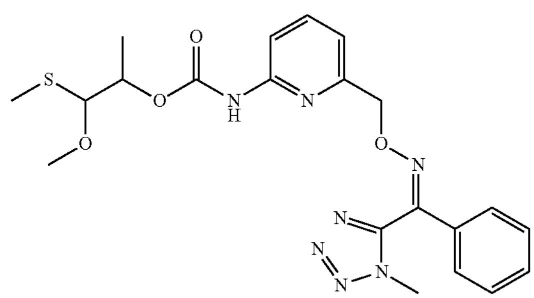 [SMILES: COC(SC)C(C)OC(=O)Nc1cccc(CO/N=C(\C(=N)N(C)N=N)c2ccccc2)n1] | |
| c-14 | 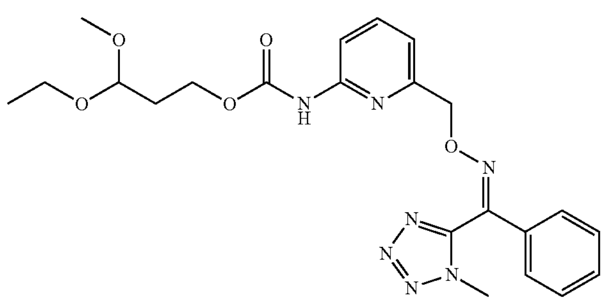 | |
| c-15 | 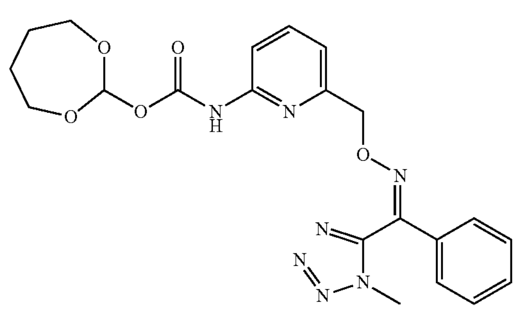 [SMILES: CN(N=N)C(=N)/C(=N\OCc1cccc(NC(=O)OC2OCCCCO2)n1)c1ccccc1] | |

TABLE 3-continued

| Compound No. | Chemical structure | Physical property ¹H-NMR |
|---|---|---|
| c-16 | 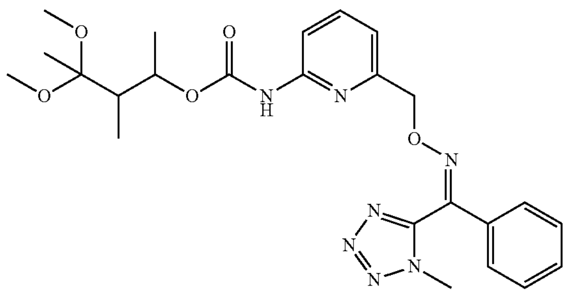 [SMILES: COC(C)(OC)C(C)C(C)OC(=O)Nc1cccc(CO/N=C(/c2ccccc2)c2nnnn2C)n1] | |
| c-17 | 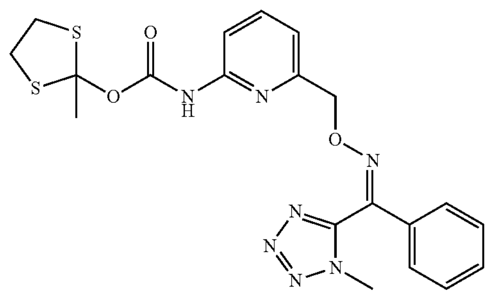 [SMILES: Cn1nnnc1/C(=N\OCc1cccc(NC(=O)OC2(C)SCCS2)n1)c1ccccc1] | |
| c-18 | 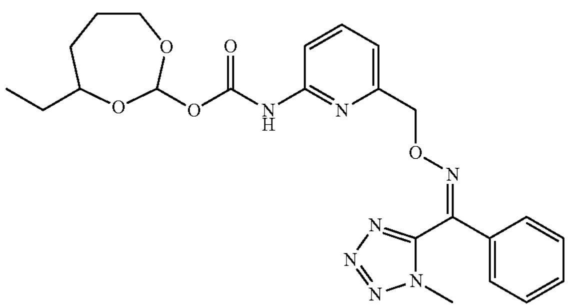 [SMILES: CCC1CCCOC(OC(=O)Nc2cccc(CO/N=C(/c3ccccc3)c3nnnn3C)n2)O1] | |
| c-19 | 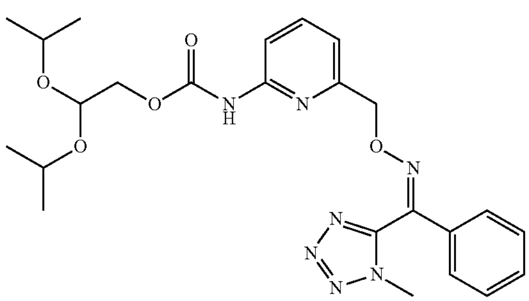 [SMILES: CC(C)OC(COC(=O)Nc1cccc(CO/N=C(/c2ccccc2)c2nnnn2C)n1)OC(C)C] | |
| c-20 | 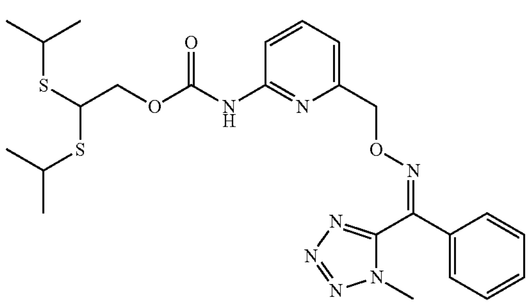 [SMILES: CC(C)SC(COC(=O)Nc1cccc(CO/N=C(/c2ccccc2)c2nnnn2C)n1)SC(C)C] | |

TABLE 3-continued

| Compound No. | Chemical structure | Physical property $^1$H-NMR |
|---|---|---|
| c-21 | 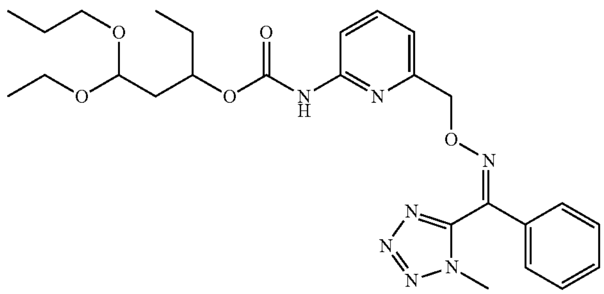 [SMILES: CCCOC(CC(CC)OC(=O)Nc1cccc(CO/N=C(/c2ccccc2)c2nnnn2C)n1)OCC] | |
| c-22 | 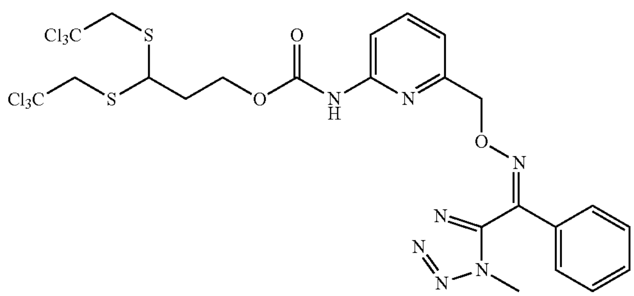 | |
| c-23 | 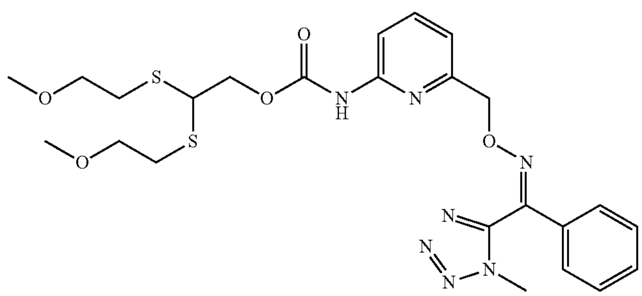 [SMILES: COCCSC(COC(=O)Nc1cccc(CO/N=C(\C(=N)N(C)N=N)c2ccccc2)n1)SCCOC] | |
| c-24 | 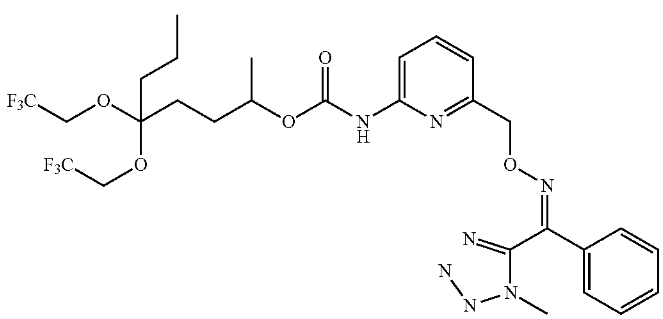 [SMILES: CCCC(CCC(C)OC(=O)Nc1cccc(CO/N=C(\C(=N)N(C)NN)c2ccccc2)n1)(OCC(F)(F)F)OCC(F)(F)F] | |
| c-25 | 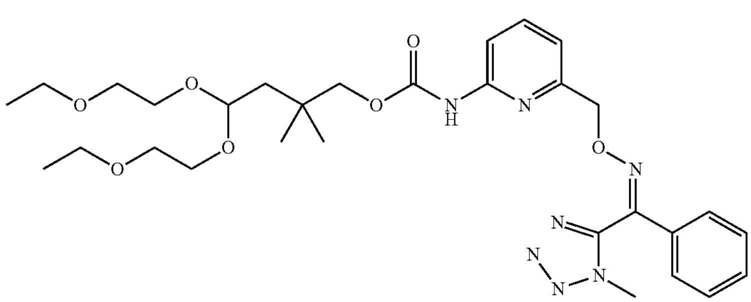 [SMILES: CCOCCOC(CC(C)(C)COC(=O)Nc1cccc(CO/N=C(\C(=N)N(C)NN)c2ccccc2)n1)OCCOCC] | |

TABLE 4

| Compound No. | Chemical structure | Physical property | ¹H-NMR |
|---|---|---|---|
| d-1 | 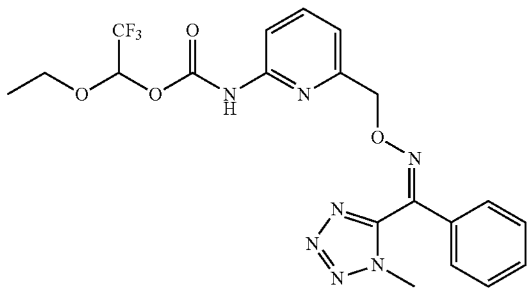 [SMILES: CCOC(OC(=O)Nc1cccc(CO/N=C(/c2ccccc2)c2nnnn2C)n1)C(F)(F)F] | mp 123-124 | — |
| d-2 | 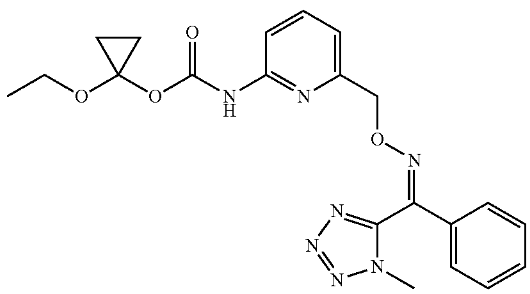 [SMILES: CCOC1(OC(=O)Nc2cccc(CO/N=C(/c3ccccc3)c3nnnn3C)n2)CC1] | AMR | 1.23-1.28 (m, 7H), 3.80 (q, 2H), 3.93 (s, 3H), 5.26 (s, 2H), 6.98 (d, 1H), 7.29 (br, 1H), 7.35-7.52 (m, 5H), 7.69 (t, 1H), 7.95 (d, 1H). |
| d-3 | 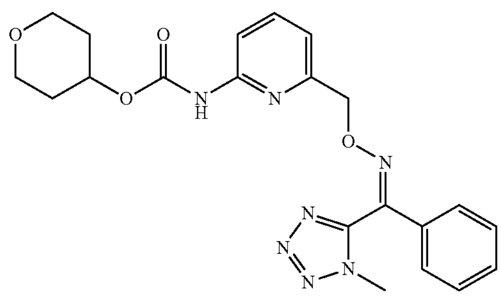 [SMILES: Cn1nnnc1/C(=N\OCc1cccc(NC(=O)OC2CCOCC2)n1)c1ccccc1] | mp 72-73 | — |
| d-4 | 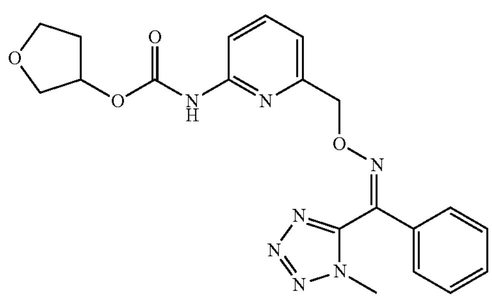 [SMILES: Cn1nnnc1/C(=N\OCc1cccc(NC(=O)OC2CCOC2)n1)c1ccccc1] | mp 76-78 | — |
| d-5 | 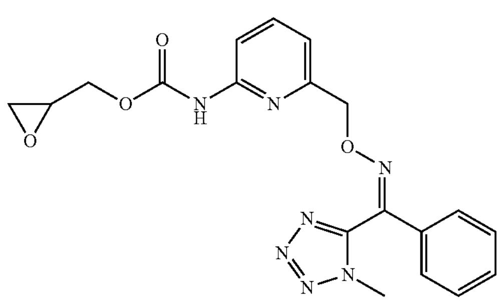 [SMILES: Cn1nnnc1/C(=N\OCc1cccc(NC(=O)OCC2CO2)n1)c1ccccc1] | AMR | 2.70 (dd, 1H, J = 5.0, 2.6 Hz), 2.88 (dd, 1H, J = 5.0, 3.9 Hz), 3.27 (dd dd, 1H, J = 6.4, 3.9, 2.9, 2.6 Hz), 3.99 (s, 3H), 4.04 (dd, 1H, J = 12.4, 6.4 Hz), 4.54 (dd, 1H, J = 12.4, 2.9 Hz), 5.27 (s, 2H), 6.98 (d, 1H, J = 7.5 Hz), 7.35-7.53 (m, 6H), 7.69 (dd, 1H, J = 8.3, 7.5 Hz), 7.88 (d, 1H, J = 8.3 Hz). |

TABLE 4-continued

| Compound No. | Chemical structure | Physical property | ¹H-NMR |
|---|---|---|---|
| d-6 | 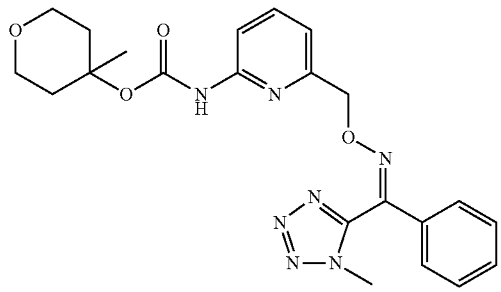 [SMILES: Cn1nnnc1/C(=N\OCc1cccc(NC(=O)OC2(C)CCOCC2)n1)c1ccccc1] | AMR | 1.58 (s, 3H), 1.71-1.81 (m, 2H), 2.18-2.23 (m, 2H), 3.67-3.74 (m, 4H), 3.98 (s, 3H), 5.26 (s, 2H), 6.95 (d, 2H), 7.26-7.53 (m, 6H), 7.65 (t, 1H), 7.86 (d, 1H). |
| d-7 | 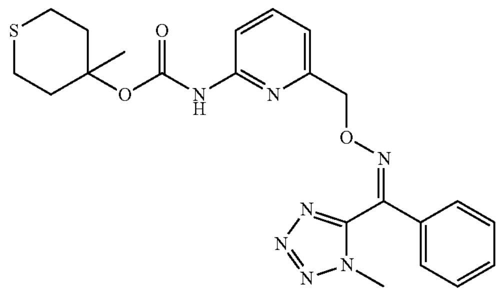 [SMILES: Cn1nnnc1/C(=N\OCc1cccc(NC(=O)OC2(C)CCSCC2)n1)c1ccccc1] | AMR | 1.22 (s, 3H), 171-1.89 (m, 4H), 2.43-2.48 (m, 2H), 2.85-2.98 (m, 2H), 3.98 (s, 3H), 5.26 (s, 2H), 6.95 (d, 1H), 7.35-7.53 (m, 6H), 7.67 (t, 1H), 7.84 (d, 1H). |
| d-8 | 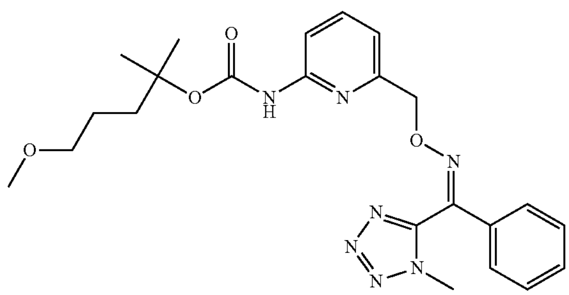 [SMILES: COCCCC(C)(C)OC(=O)Nc1cccc(CO/N=C(/c2ccccc2)c2nnnn2C)n1] | AMR | 1.52 (s, 6H), 1.63-1.70 (m, 2H), 1.83-1.88 (m, 2H), 3.34 (s, 3H), 3.39 (t, 2H), 3.98 (s, 3H), 5.24 (s, 2H), 6.93 (d, 1H), 7.15 (br-s, 1H), 7.35-7.53 (m, 5H), 7.65 (t, 1H), 7.85 (d, 1H) |
| d-9 | 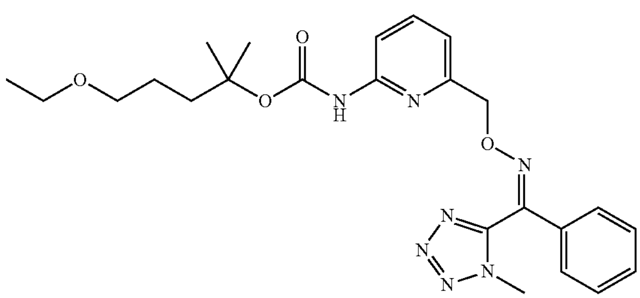 [SMILES: CCOCCCC(C)(C)OC(=O)Nc1cccc(CO/N=C(/c2ccccc2)c2nnnn2C)n1] | AMR | 1.20 (t, 3H, J = 7.0 Hz), 1.52 (s, 6H), 1.63-1.71 (m, 2H), 1.83-1.88 (m, 2H), 3.42 (t, 2H, J = 6.7 Hz), 3.47 (q, 2H, J = 7.0 Hz), 3.98 (s, 3H), 5.24 (s, 2H), 6.93 (d, 1H, J = 7.0 Hz), 7.16 (br-s, 1H), 7.35-7.53 (m, 5H), 7.65 (dd, 1H, J = 8.3, 7.0 Hz), 7.85 (d, 1H, J = 8.3 Hz). |
| d-10 | 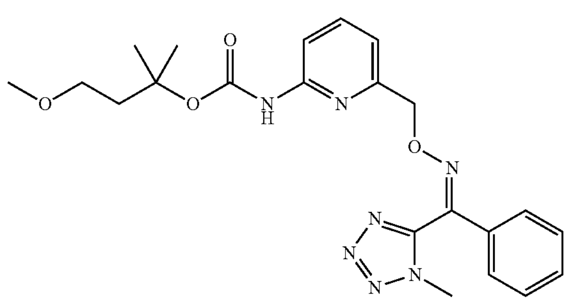 [SMILES: COCCC(C)(C)OC(=O)Nc1cccc(CO/N=C(/c2ccccc2)c2nnnn2C)n1] | AMR | 1.55 (s, 6H), 2.12 (t, 2H, J = 7.0 Hz), 3.33 (s, 3H), 3.51 (t, 2H, J = 7.0 Hz), 3.98 (s, 3H), 5.25 (s, 2H), 6.94 (d, 1H, J = 7.5 Hz), 7.18 (br-s, 1H), 7.35-7.53 (m, 5H), 7.66 (dd, 1H, J = 8.2, 7.5 Hz), 7.86 (d, 1H, J = 8.2 Hz). |

TABLE 4-continued

| Compound No. | Chemical structure | Physical property | ¹H-NMR |
|---|---|---|---|
| d-11 | 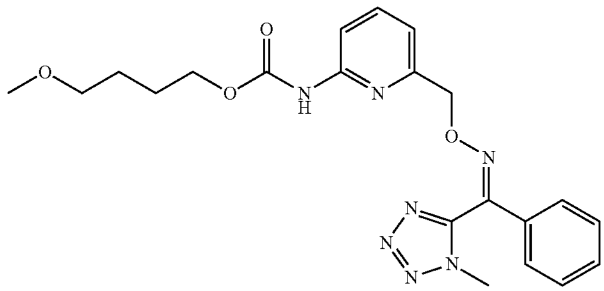 | AMR | 1.60-1.80 (m, 4H), 3.34 (s, 3H), 3.42 (t, 2H, J = 6.1 Hz), 3.98 (s, 3H), 4.21 (t, 2H, J = 6.4 Hz), 5.26 (s, 2H), 6.95 (d, 1H, J = 7.5 Hz), 7.29 (br-s, 1H), 7.35-7.45 (m, 3H), 7.50-7.53 (m, 2H), 7.68 (dd, 1H, J = 8.2, 7.5 Hz), 7.89 (d, 1H, J = 8.2 Hz). |
| d-12 | 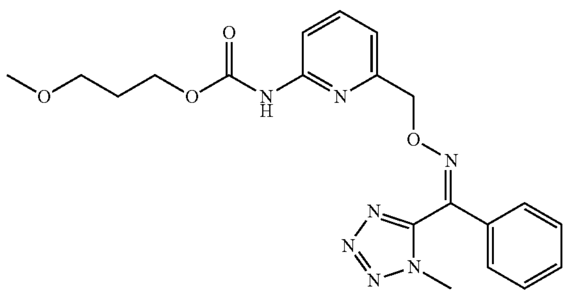 [SMILES: COCCCOC(=O)Nc1cccc(CO/N=C(/c2ccccc2)c2nnnn2C)n1] | AMR | 1.96 (tt, 2H, J = 6.5, 6.2 Hz), 3.35 (s, 3H), 3.48 (t, 2H, J = 6.2 Hz), 3.98 (s, 3H), 4.28 (t, 2H, J = 6.5 Hz), 5.26 (s, 2H), 6.95 (d, 1H, J = 7.4 Hz), 7.32 (br-s, 1H), 7.35-7.53 (m, 5H), 7.68 (dd, 1H, J = 8.2, 7.4 Hz), 7.90 (d, 1H, J = 8.2 Hz). |
| d-13 | 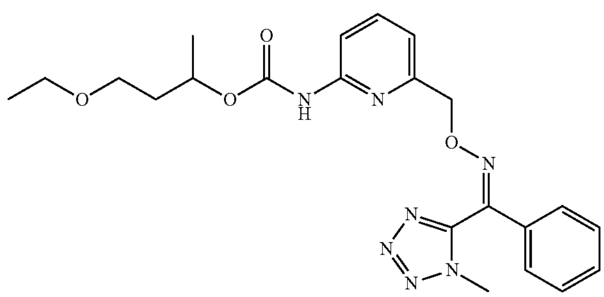 [SMILES: CCOCCC(C)OC(=O)Nc1cccc(CO/N=C(/c2ccccc2)c2nnnn2C)n1] | AMR | 1.18 (t, 3H, J = 7.0 Hz), 1.33 (d, 3H, J = 6.4 Hz), 1.83-1.94 (m, 2H), 3.45 (t, 2H, J = 7.0 Hz), 3.48 (q, 2H, J = 7.0 Hz), 3.98 (s, 3H), 5.03-5.09 (m, 1H), 5.26 (s, 2H), 6.95 (d, 1H, J = 7.4 Hz), 7.24 (br-s, 1H), 7.35-7.53 (m, 5H), 7.68 (dd, 1H, J = 8.1, 7.4 Hz), 7.90 (d, 1H, J = 8.1 Hz). |
| d-14 | 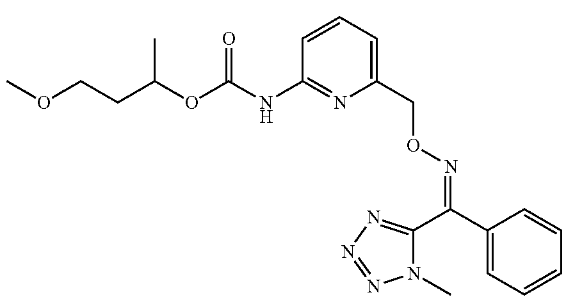 [SMILES: COCCC(C)OC(=O)Nc1cccc(CO/N=C(/c2ccccc2)c2nnnn2C)n1] | AMR | 1.33 (d, 3H, J = 6.2 Hz), 1.78-1.96 (m, 2H), 3.32 (s, 3H), 3.45 (t, 2H, J = 6.4 Hz), 3.98 (s, 3H), 5.02-5.08 (m, 1H), 5.26 (s, 2H), 6.95 (d, 1H, J = 7.3 Hz), 7.23 (br-s, 1H), 7.35-7.54 (m, 5H), 7.68 (dd, 1H, J = 8.2, 7.3 Hz), 7.90 (d, 1H, J = 8.2 Hz). |
| d-15 | 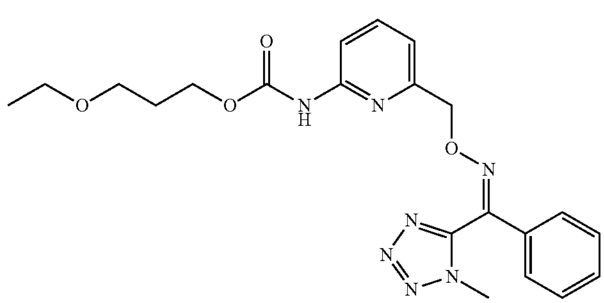 | VISC. OIL | 1.20 (t, 3H, J = 7.0 Hz), 1.96 (tt, 2H, J = 6.4, 6.4 Hz), 3.48 (q, 2H, J = 7.0 Hz), 3.52 (t, 2H, J = 6.4 Hz), 3.98 (s, 3H), 4.29 (t, 2H, J = 6.4 Hz), 5.26 (s, 2H), 6.95 (d, 1H, J = 7.5 Hz), 7.29 (br-s, 1H), 7.35-7.54 (m, 5H), 7.68 (dd, 1H, J = 8.1, 7.5 Hz), 7.90 (d, 1H, J = 8.1 Hz). |

TABLE 4-continued

| Compound No. | Chemical structure | Physical property | $^1$H-NMR |
|---|---|---|---|
| d-16 | 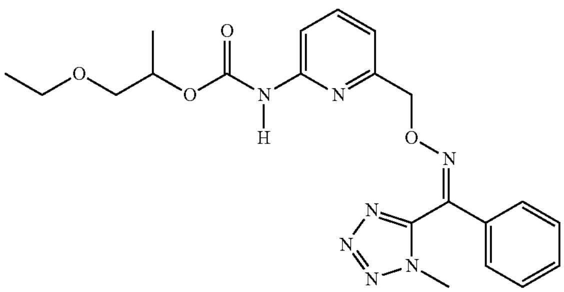 [SMILES: CCOCC(C)OC(=O)Nc1cccc(CO/N=C(/c2ccccc2)c2nnnn2C)n1] | AMR | 3 (upper):1 (lower) mixture; upper molecule 1.21 (t, 3H, J = 7.0 Hz), 1.31 (d, 3H, J = 6.6 Hz), 3.48-3.60 (m, 4H), 3.98 (s, 3H), 5.06-5.10 (m, 1H), 5.25 (s, 2H), 6.95 (d, 1H, J = 7.4 Hz), 7.30 (br-s, 1H), 7.35-7.53 (m, 5H), 7.67 (dd, 1H, J = 8.4, 7.4 Hz), 7.90 (d, 1H, J = 8.4 Hz). |
| | | | lower molecule 1.21 (t, 3H, J = 7.0 Hz), 1.21 (d, 3H, J = 6.4 Hz), 3.48-3.60 (m, 2H), 3.98 (s, 3H), 4.10-4.19 (m, 1H), 5.06-5.10 (m, 1H), 5.26 (s, 2H), 6.96 (d, 1H, J = 7.7 Hz), 7.30 (br-s, 1H), 7.35-7.53 (m, 5H), 7.68 (dd, 1H, J = 8.4, 7.7 Hz), 7.90 (d, 1H, J = 8.4 Hz). |
| d-17 | 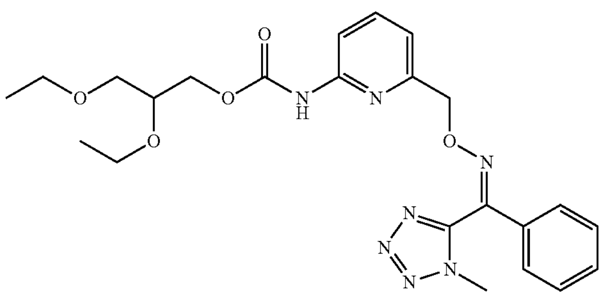 [SMILES: CCOCC(COC(=O)Nc1cccc(CO/N=C(/c2ccccc2)c2nnnn2C)n1)OCC] | VISC. OIL | 1.16-1.26 (m, 6H), 3.47-3.72 (m, 7H), 3.97 (s, 3H), 4.23 (dd, 1H), 4.36 (dd, 1H), 5.28 (s, 2H), 6.97 (d, 1H), 7.34-7.51 (m, 5H), 7.69 (dd, 1H), 7.91 (d, 1H) |
| d-18 | 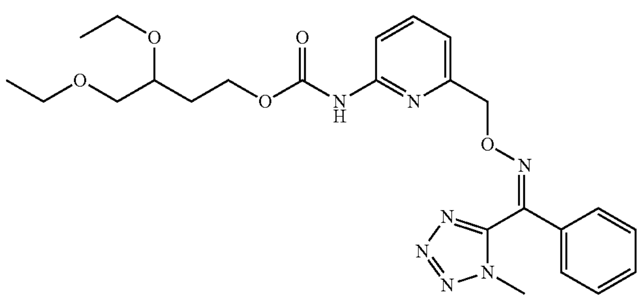 [SMILES: CCOCC(CCOC(=O)Nc1cccc(CO/N=C(/c2ccccc2)c2nnnn2C)n1)OCC] | VISC. OIL | 1.61-1.22 (m, 6H), 1.84-1.98 (m, 2H), 3.44-3.55 (m, 6H), 3.66-3.71 (m, 1H), 3.97 (s, 3H), 4.30 (d, 1H), 4.33 (d, 1H), 5.27 (s, 2H), 6.96 (d, 1H), 7.34-7.51 (m, 5H), 7.68 (dd, 1H), 7.90 (d, 1H) |
| d-19 | 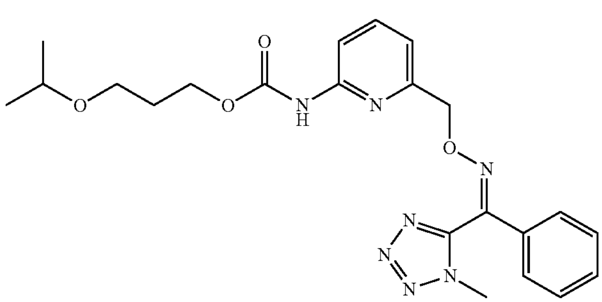 [SMILES: CC(C)OCCCOC(=O)Nc1cccc(CO/N=C(/c2ccccc2)c2nnnn2C)n1] | | |

TABLE 4-continued

| Compound No. | Chemical structure | Physical property | ¹H-NMR |
|---|---|---|---|
| d-20 | 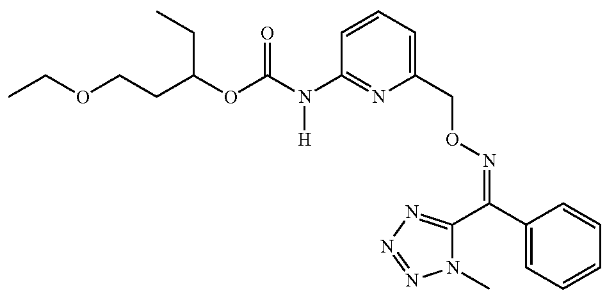 [SMILES: CCOCCC(CC)OC(=O)Nc1cccc(CO/N=C(/c2ccccc2)c2nnnn2C)n1] | | |
| d-21 | 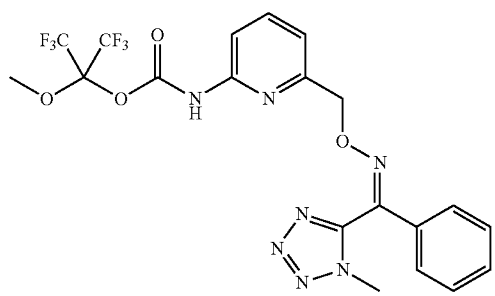 [SMILES: COC(OC(=O)Nc1cccc(CO/N=C(/c2ccccc2)c2nnnn2C)n1)(C(F)(F)F)C(F)(F)F] | | |
| d-22 | 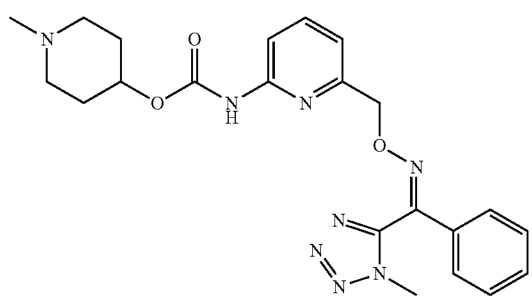 [SMILES: CN1CCC(OC(=O)Nc2cccc(CO/N=C(\C(=N)N(C)N=N)c3ccccc3)n2)CC1] | | |

TABLE 5

| Compound No. | Chemical Structure | Physical property | ¹H-NMR |
|---|---|---|---|
| e-1 | 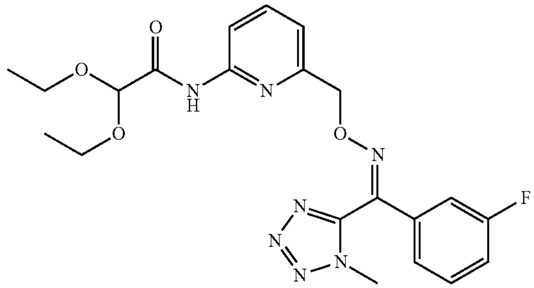 [SMILES: CCOC(OCC)C(=O)Nc1cccc(CO/N=C(/c2cccc(F)c2)c2nnnn2C)n1] | nD20.5 — 1.5457 | |

TABLE 5-continued

| Compound No. | Chemical Structure | Physical property $^1$H-NMR |
|---|---|---|
| e-2 | 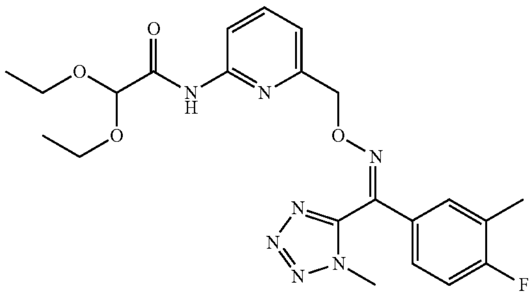 [SMILES: CCOC(OCC)C(=O)Nc1cccc(CO/N=C(/c2ccc(F)c(C)c2)c2nnnn2C)n1] | AMR 1.31 (t, 6H), 2.46 (s, 3H), 3.64-3.75 (m, 4H), 3.95 (s, 3H), 4.87 (s, 1H), 5.25 (s, 2H), 6.91 (d, 1H), 6.98 (t, 1H), 7.28-7.36 (m, 3H), 7.50 (br-s, 1H), 7.65 (t, 1H), 7.86 (d, 1H). |
| e-3 | 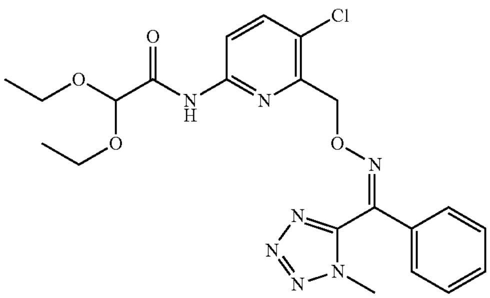 [SMILES: CCOC(OCC)C(=O)Nc1ccc(Cl)c(CO/N=C(/c2ccccc2)c2nnnn2C)n1] | AMR 1.30 (t, 6H, J = 7.0 Hz), 3.67-3.76 (m, 4H), 4.04 (s, 3H), 4.93 (s, 1H), 543 (s, 2H), 7.35-7.48 (m, 3H), 7.51-7.54 (m, 2H), 7.71 (d, 1H, J = 8.8 Hz), 8.23 (d, 1H, J = 8.8 Hz), 8.92 (br-s, 1H). |

Next, although the following briefly indicates preparation examples of the fungicide according to the present invention, the additives used and proportions thereof are not limited to the examples, and may be varied over a wide range. Furthermore, the term "part (s)" in the preparation examples refers to part (s) by mass.

Preparation Example 1

Wettable Powder

| | |
|---|---|
| Compound according to the present invention | 40 parts |
| Clay | 53 parts |
| Sodium dioctylsulfosuccinate | 4 parts |
| Sodium lignin sulfonate | 3 parts |

The above components were uniformly mixed and finely crushed to obtain a wettable powder containing 40% of the active ingredient.

Preparation Example 2

Emulsion

| | |
|---|---|
| Compound according to the present invention | 10 parts |
| Solvesso 200 | 53 parts |
| Cyclohexanone | 26 parts |
| Calcium dodecylbenzenesulfonate | 1 part |
| Polyoxyethylene alkyl allyl ether | 10 parts |

The above components were mixed and dissolved to obtain an emulsion containing 10% of the active ingredient.

Preparation Example 3

Powder

| | |
|---|---|
| Compound according to the present invention | 10 parts |
| Clay | 90 parts |

The above components were uniformly mixed and finely crushed to obtain a powder containing 10% of the active ingredient.

Preparation Example 4

Granules

| | |
|---|---|
| Compound according to the present invention | 5 parts |
| Clay | 73 parts |
| Bentonite | 20 parts |
| Sodium dioctylsulfosuccinate | 1 part |
| Potassium phosphate | 1 part |

The above components were crushed and mixed well followed by the addition of water, kneading well, granulating, and drying, to obtain granules containing 5% of the active ingredient.

Preparation Example 5

Suspension

| | |
|---|---|
| Compound according to the present invention | 10 parts |
| Polyoxyethylene alkyl allyl ether | 4 parts |
| Sodium polycarbonate | 2 parts |
| Glycerin | 10 parts |
| Xanthan gum | 0.2 parts |
| Water | 73.8 parts |

The above components were mixed followed by wet-milling to a particle diameter of 3 microns or less to obtain a suspension containing 10% of the active ingredient.

Preparation Example 6

Water-Dispersible Granules

| | |
|---|---|
| Compound according to the present invention | 40 parts |
| Clay | 36 parts |
| Potassium chloride | 10 parts |
| Sodium alkylbenzenesulfonate | 1 part |
| Sodium lignin sulfonate | 8 parts |
| Formaldehyde condensation product of sodium alkylbenzenesulfonate | 5 parts |

The above components were uniformly mixed and finely crushed followed by adding a suitable amount of water and kneading to form a clay-like mixture. The clay-like mixture was granulated and then dried to obtain water-dispersible granules containing 40% of the active ingredient.

Test Example 1

Tomato Late Blight (PN) Control Test

The aforementioned emulsion of Preparation Example 2 was sprayed at an active ingredient concentration of 100 ppm onto tomato seedlings (variety: Regina, leaf stage: 4 to 5) cultivated in unglazed pots. After spraying, the seedlings were allowed to air-dry at room temperature and inoculated by spraying with a suspension of zoosporangia of tomato late blight pathogen (*Phytophthora infestans*) followed by holding for 4 days in a constant temperature room (20° C.) at high humidity using a 12 hour light/dark cycle. The appearance of lesions on the leaves was compared with an untreated group to determine control effects (control value).

When the tomato late blight control test was carried out using the compounds of compound numbers a-1 to a-4, a-6 to a-33, b-1 to b-1, c-1 to c-12, d-1 to d-18 and e-1 to e-3, all of the compounds demonstrated control values of 70% or more. The compound numbers correspond to the compound numbers of Tables 1 to 5.

Control value (%)=[(incidence in untreated group−incidence in treated group)/(incidence in untreated group)×100

Test Example 2

Cucumber Damping-Off (PU) Control Test 40 ml of sterile soil were placed in plastic cups followed by leveling the surface of the soil. The soil was then irrigated with 30 ml of the aforementioned emulsion of Preparation Example 2 at an active ingredient concentration of 100 ppm. Following irrigation, cucumbers (variety: Sagami Hanjiro) were planted in the soil and covered with 20 ml of contaminated soil (containing *Pythium ultimum*) from above. The cups were then placed in plastic bags and allowed to stand undisturbed for 3 days in a constant temperature room at 25° C. (dark location under greenhouse conditions). Next, the plants were removed from the bags and held in a constant temperature room at 25° C. using a light-dark cycle of 12 hours. On day 7 after planting, the ratios of healthy seedlings were compared between an untreated group and treated group to calculate control effects (control values).

When the cucumber damping-off control test was carried out using the compounds of compound numbers a-1 to a-4, a-6 to a-9, a-14, a-17, a-18, a-20 to a-23, a-25 to a-31, a-33, b-3, b-8 to b-11, c-1, c-4 to c-10, d8 to d10 and d-13 to d-18, all of the compounds demonstrated control values of 50% or more. The compound numbers correspond to the compound numbers of Tables 1 to 5.

Test Example 3

Antimicrobial Test

The compound according to the present invention was dissolved in dimethylsulfoxide and diluted to double the prescribed concentration in a 96-well microplate using PSY medium to obtain a drug solution. On the other hand, a diluted dimethylsulfoxide solution was prepared using PSY medium for use as an untreated group.

A suspension of liquid-cultured test microorganisms (*Pythium aphanidermatum*) was mixed with an equal volume of the drug solution and cultured in a dark location at 25° C. Mycelia growth was observed on days 3 to 7 of culturing to determine mycelia growth inhibition rates.

When the antimicrobial test was carried out using the compounds of compound numbers a-1 to a-7, a-9 to a-12, a-14, a-15, a-17 to a-20, a-22 to a-31, a-33, b-1, b-3 to b-8, b-10, b-1, c-1 to c-12, d-1, d3 to d6, d-8, d-9, d-11 to d-18 and e-1 to e-3, all of the compounds demonstrated mycelia growth inhibition rates of 50% or more at a compound concentration of 1 ppm. The compound numbers correspond to the compound numbers of Tables 1 to 5.

As shown above, the tetrazolyloxime derivative and the salt thereof according to the present invention can be understood to demonstrate superior plant disease control effects.

INDUSTRIAL APPLICABILITY

The tetrazolyloxime derivative and the salt thereof according to the present invention exhibit superior control effects against plant diseases without concerns over chemical damage to useful plants. Since the fungicide according to the present invention contains at least one selected from the group consisting of the tetrazolyloxime derivatives and the salts thereof according to the present invention, control effects thereof are effective in the cultivation of agricultural crops without causing chemical damage to crops or contaminating the environment, and the toxicity thereof with respect to humans, livestock and fish is low. Thus, the present invention is extremely industrially useful.

The invention claimed is:

1. A tetrazolyloxime derivative represented by formula (1), or a salt thereof:

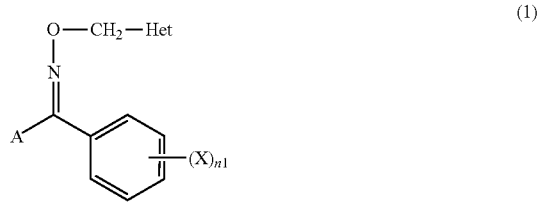

in formula (1),
X represents a halogen atom, a C1-8 alkyl group, a C1-8 alkoxy group, a cyano group, a C1-8 alkylsulfonyl group, a nitro group, a C1-8 haloalkyl group, or an unsubstituted or substituted aryl group, n1 indicates a number of X and represents an integer of 0 to 5, and X is mutually identical or different when n1 is at least 2;
A represents a tetrazolyl group represented by formula (2) or formula (3):

in formula (2) and formula (3), Y represents a C1-8 alkyl group, and asterisks indicate bonding sites;
Het represents a group represented by formula (4) or formula (5):

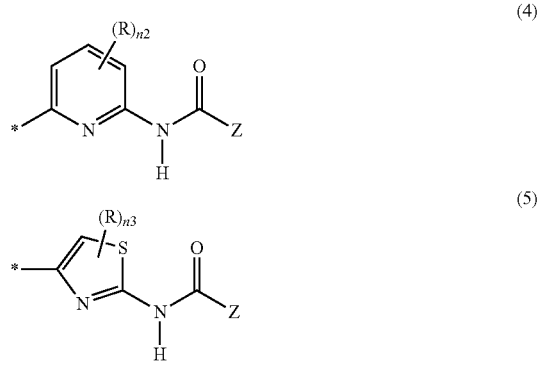

in formula (4) and formula (5), asterisks represent bonding sites;
R represents a halogen atom, a cyano group, a nitro group, a hydroxyl group, a thiol group, a formyl group, a carboxyl group, an unsubstituted or substituted amino group, an unsubstituted or substituted C1-8 alkyl group, an unsubstituted or substituted C2-8 alkenyl group, an unsubstituted or substituted C2-8 alkynyl group, an unsubstituted or substituted aryl group, an unsubstituted or substituted heterocyclic group, $OR^1$, $S(O)_m R^1$, $COR^1$ or $CO_2 R^1$, $R^1$ represents an unsubstituted or substituted amino group, an unsubstituted or substituted C1-8 alkyl group, an unsubstituted or substituted C3-8 cycloalkyl group, an unsubstituted or substituted C2-8 alkenyl group, an unsubstituted or substituted C2-8 alkynyl group, an unsubstituted or substituted aryl group, or an unsubstituted or substituted heterocyclic group, and m indicates a number of oxygen atoms in parentheses and represents an integer of 0 to 2;
n2 in formula (4) indicates a number of R and represents an integer of 0 to 3, and a plurality of the R groups are mutually identical or different when n2 is at least 2;
n3 in formula (5) indicates a number of R and represents 0 or 1;
Z in formula (4) and formula (5) represents a group represented by formula (Z-1):

in formula (Z-1), asterisks represent bonding sites;
E represents a single bond or a C1-8 alkylene chain;
$R^{2a}$ and $R^{2b}$ respectively and independently represent a C1-8 alkoxy group, a C1-8 haloalkoxy group, a C1-8 alkoxy C1-8 alkoxy group, a C1-8 alkylthio group, a C1-8 haloalkylthio group or a C1-8 alkoxy C1-8 alkylthio group; and
$R^3$ represents a hydrogen atom or a C1-8 alkyl group.

2. A tetrazolyloxime derivative or a salt thereof, according to claim 1, wherein the tetrazolyloxime derivative is represented by formula (6):

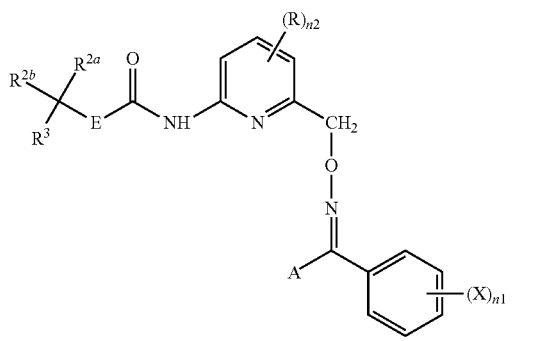

in formula (6), X, n1, A, R, n2, E, $R^{2a}$, $R^{2b}$ and $R^3$ are each the same as defined in claim 1.

3. A fungicide comprising, as an active ingredient thereof, at least one selected from the group consisting of the tetrazolyloxime derivative and the salt thereof according to claim 1 or claim 2.

* * * * *